United States Patent
Conklin et al.

(10) Patent No.: US 11,020,463 B2
(45) Date of Patent: Jun. 1, 2021

(54) METHOD OF DETERMINING CELLULAR PROTEIN HOMEOSTASIS

(71) Applicants: The J. David Gladstone Institutes, a testamentary trust established under the Will of J. David Gladstone, San Francisco, CA (US); The Regents of the University of California, Oakland, CA (US)

(72) Inventors: Bruce R. Conklin, San Francisco, CA (US); Luke Judge, San Francisco, CA (US)

(73) Assignees: The J. David Gladstone Institutes, San Francisco, CA (US), a testamentantary trust established under the Will of J. David Gladstone; The Regents of the University of California, Oakland, CA (US)

(*) Notice: Subject to any disclaimer, the term of this patent is extended or adjusted under 35 U.S.C. 154(b) by 531 days.

(21) Appl. No.: 15/750,495

(22) PCT Filed: Aug. 8, 2016

(86) PCT No.: PCT/US2016/046023
§ 371 (c)(1),
(2) Date: Feb. 5, 2018

(87) PCT Pub. No.: WO2017/027466
PCT Pub. Date: Feb. 16, 2017

(65) Prior Publication Data
US 2019/0015486 A1    Jan. 17, 2019

Related U.S. Application Data

(60) Provisional application No. 62/202,339, filed on Aug. 7, 2015.

(51) Int. Cl.

| | | |
|---|---|---|
| *A61K 38/57* | (2006.01) | |
| *G01N 33/50* | (2006.01) | |
| *C12Q 1/6881* | (2018.01) | |
| *A61K 35/00* | (2006.01) | |
| *C12N 5/077* | (2010.01) | |
| *C12Q 1/24* | (2006.01) | |

(52) U.S. Cl.
CPC ............. *A61K 38/57* (2013.01); *A61K 35/00* (2013.01); *C12N 5/0658* (2013.01); *C12Q 1/24* (2013.01); *C12Q 1/6881* (2013.01); *G01N 33/5014* (2013.01); *G01N 33/5061* (2013.01); *G01N 33/5073* (2013.01); *C12Q 2600/106* (2013.01); *C12Q 2600/142* (2013.01); *C12Q 2600/156* (2013.01)

(58) Field of Classification Search
CPC .................................................. A61K 38/57
USPC ......................................................... 506/10
See application file for complete search history.

(56) References Cited

U.S. PATENT DOCUMENTS

| 8,257,941 B2 | 9/2012 | Sakurada et al. |
| 2003/0036195 A1 | 2/2003 | Studer et al. |
| 2013/0189785 A1 | 7/2013 | Palecek et al. |
| 2015/0140662 A1 | 5/2015 | Okita et al. |

FOREIGN PATENT DOCUMENTS

| EP | 3332020 | 6/2018 |
| WO | 2017027466 | 2/2017 |

OTHER PUBLICATIONS

Arakawa A et al. (2010) "The C-terminal BAG domain of BAG5 induces conformational changes of the Hsp70 nucleotide-binding domain for ADP-ATP exchange"; Structure 18; pp. 309-319.
Bockorny et al. (2012) "Severe heart failure after bortezomib treatment in a patient with multiple myeloma: a case report and review of the literature." ; Acta Haematol 128; pp. 244-247.
Eadon, et al (2013) "Genetic and epigenetic variants contributing to clofarabine cytotoxicity"; Hum Mol Genet. 22(19); pp. 4007-4020.
Favatier, et al (1997) "Variation in hsp gene expression and Hsp polymorphism: do they contribute to differential disease susceptibility and stress tolerance?"; Cell Stress Chaperones 2(3); pp. 141-155.
Hindson BJ et al. (2011) "High-throughput droplet digital PCR system for absolute quantitation of DNA copy number"; Anal Chem 83: pp. 8604-8610.
Hishiya, et al. (2011) "BAG3 directly interacts with mutated alphaB-crystallin to suppress its aggregation and toxicity"; PLoS One 6(3):e16828.
Homma S et al. (2006) "BAG3 deficiency results in fulminant myopathy and early lethality"; Am J Pathol 169: pp. 761-773.
Huebsch N et al. (2015) "Automated Video-Based Analysis of Contractility and Calcium Flux in Human-Induced Pluripotent Stem Cell-Derived Cardiomyocytes Cultured over Different Spatial Scales"; Tissue Eng Part C Methods 21: pp. 467-479.
Judge, et al (2017) "A BAG3 chaperone complex maintains cardiomyocyte function during proteotoxic stress"; JCI Insight 2(14); pp. 1-17.
Lian et al (2012) "Directed cardiomyocyte differentiation from human pluripotent stem cells by modulating Wnt/β-catenin signaling under fully defined conditions"; Nat Protoc.8(1): pp. 162-175.
Maniratanachote, et al. (2005) "Chaperone proteins involved in troglitazone-induced toxicity in human hepatoma cell lines"; Toxicol Sci. 83(2); pp. 293-302.

(Continued)

*Primary Examiner* — Karla A Dines

(74) *Attorney, Agent, or Firm* — Schwegman Lundberg & Woessner, P.A.

(57) ABSTRACT

The present invention provides assays and compositions to identify the risk of toxicity in a patient population with genotypic variations in specific proteins and/or protein complexes within the patient population.

7 Claims, 11 Drawing Sheets

(56) References Cited

OTHER PUBLICATIONS

Maddah et al. (2015) "A non-invasive platform for functional characterization of stem-cell-derived cardiomyocytes with applications in cardiotoxicity testing"; Stem Cell Reports, 4(4): pp. 621-631.
McCormick M. (1987) "Sib selection"; Methods Enzymol 151: pp. 445-449.
Nardai, et al (2006) "Chaperone-related immune dysfunction: an emergent property of distorted chaperone networks"; Trends Immunol. 27(2); pp. 74-79.
Rauch JN et al. (2014) "Binding of human nucleotide exchange factors to heat shock protein 70 (Hsp70) generates functionally distinct complexes in vitro"; J Biol Chem 289(3): pp. 1402-1414.
Scott, et al. (2013) "Human induced pluripotent stem cells and their use in drug discovery for toxicity testing"; Toxicol Lett. 219(1); pp. 49-58.
Watanabe, et al (2014) "Activation of the ubiquitin-proteasome system against arsenic trioxide cardiotoxicity involves ubiquitin ligase Parkin for mitochondrial homeostasis."; Toxicology 322; pp. 43-50.
"European Application Serial No. 16835754.9, Communication Pursuant to Article 94(3) EPC dated Sep. 11, 2020", 5 pgs.
"European Application Serial No. 16835754.9, Response filed Jun. 29, 2020 to Communication Pursuant to Article 94(3) EPC dated Feb. 19, 2020", 24 pgs.
Yuichiro, Miyaoka, et al., "Isolation of single-base genome-edited human iPS cells without antibiotic selection", Nature Methods, vol. 11, No. 3, (Mar. 1, 2014), 291-293.
"European Application Serial No. 16835754.9, Communication Pursuant to Article 94(3) EPC dated Feb. 19, 2020", 3 pgs.
"International Application Serial No. PCT US2016 046023, International Search Report dated Dec. 28, 2016", 4 pgs.
"International Application Serial No. PCT US2016 046023, Written Opinion dated Dec. 28, 2016", 9 pgs.
"International Application Serial No. PCT US2016 046023, International Preliminary Report on Patentability dated Feb. 22, 2018", 11 pgs.
"European Application Serial No. 16835754.9, Partial Supplementary European Search Report dated Dec. 21, 2018", 15 pgs.
"European Application Serial No. 16835754.9, Extended European Search Report dated Apr. 3, 2019", 14 pgs.
"European Application Serial No. 16835754.9, Response to Communication pursuant to Rules 161(1) and 162 EPC filed Sep. 24, 2018", 9 pgs.
"European Application Serial No. 16835754.9, Response filed Oct. 21, 2019 to Extended European Search Report dated Apr. 3, 2019", 13 pgs.
"European Application Serial No. 16835754.9, Response filed Mar. 19, 2021 to Communication Pursuant to Article 94(3) EPC dated Sep. 11, 2020", 8 pgs.

METHOD OF DETERMINING CELLULAR PROTEIN HOMEOSTASIS

CROSS REFERENCE TO RELATED APPLICATIONS

This application is a national phase filing under 35 U.S.C. 371 of International Patent Application No. PCT/US2016/046023, filed Aug. 8, 2016, which claims the benefit of priority to U.S. Provisional Patent Application No. 62/202,339, filed Aug. 7, 2015.

GOVERNMENT SUPPORT

This invention was made with government support under Grant Nos. U01 HL100406 and U01 HL098179 awarded by the National Institutes of Health. The government has certain rights in the invention.

FIELD OF THE INVENTION

This invention relates to compositions and assays for the identification of risk of toxicity in response to agents in patient populations with specific genotypes.

BACKGROUND OF THE INVENTION

In the following discussion certain articles and processes will be described for background and introductory purposes. Nothing contained herein is to be construed as an "admission" of prior art. Applicant expressly reserves the right to demonstrate, where appropriate, that the articles and processes referenced herein do not constitute prior art under the applicable statutory provisions.

For many decades, clinicians have been aware of the formation of insoluble protein aggregates in particular diseases. Cells depend upon a complex network of molecular chaperones that assist proteins in folding and help stabilize the transient conformations that proteins adapt for trafficking across membranes and during their assembly and disassembly into functional complexes (Large et al. (2009) *Biochem Soc Trans* 37: 46-51; Willis M S et al. (2009) *Cardiovasc Res* 81: 439-448). It is known that different physiological and pathological conditions may overwhelm the homeostatic capability of the chaperone network and favor protein aggregation, making the refolding activity of chaperones insufficient to maintain proteome stability and prevent proteotoxicity. Under these conditions, cells count on proteolytic systems to eliminate the unstable proteins to prevent further aggregation and toxicity (Willis, id).

The lysosomal system and the ubiquitin/proteasome system (UPS), the two main proteolytic systems in cells, along with the molecular chaperones, constitute essential components of the cellular quality control systems. These systems maintain the homeostasis between proteins in their folded and unfolded states, and ensure a healthy balance within the proteome of individual cells.

Improved predictive systems for identifying individuals at risk for agent-induced toxicities, such as those exhibited when protein homeostasis and stability to the proteome are compromised, are needed by the pharmaceutical and biotechnology industries to decrease late-stage attrition in drug development and reduce the incidence of serious adverse events due to agent-induced cell toxicity. The present methods and compositions address this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings, and as set forth in the examples and appended claims.

The invention provides a method of determining risk of agent-induced toxicity in a patient population comprising providing one or more cell populations produced from clonal expansion and differentiation of an individual cell, wherein the cell populations are representative of genotypes of a gene of interest in a patient population; contacting said cell populations with an agent; and detecting ex vivo activity associated with toxicity resulting from contact with the agent, thereby detecting genotypes that are associated with an increased risk of agent-induced toxicity in a patient population with a genotype of the gene of interest.

The present invention also provides an assay for determining risk of agent-induced toxicity from administration of an agent, comprising providing one or more cell populations produced from differentiated pluripotent stem cells (PSCs), wherein the cell populations are representative of genotypes of proteins of a chaperone complex; contacting said cell populations with an agent; and detecting ex vivo activity associated with toxicity resulting from administration of the agent, thereby detecting genotypes of the chaperone complex associated with an increased risk of agent-induced toxicity in a patient population. Preferably, the cell populations are produced from the expansion of one or a small number of genetically modified cells. Preferably the cell populations are isogenic.

The present invention also provides an assay for determining risk of agent-induced toxicity from administration of an agent, comprising providing a panel of cell populations produced from differentiated pluripotent stem cells (PSCs), wherein the cell populations of the panel are representative of different genotypes of proteins of one or more chaperone complexes; contacting the panel of cell populations with an agent; and detecting ex vivo activity associated with toxicity resulting from administration of the agent, thereby detecting genotypes of the one or more chaperone complexes associated with an increased risk of agent-induced toxicity in a patient population. Preferably, the panel of cell populations comprises cell populations produced from the expansion of one or a small number of genetically modified cells. Preferably the cell populations of the panel are isogenic.

hi a specific embodiment, the invention provides an assay for determining risk of agent-induced toxicity from administration of an agent, comprising providing one or more cell populations produced from differentiated pluripotent stem cells (PSCs), wherein the cell populations comprise a mutation and/or polymorphism of the BAG3 chaperone complex; contacting said cell population(s) with an agent; and detecting ex vivo activity associated with toxicity resulting from administration of the agent, thereby detecting a genotype of the BAG3 chaperone complex associated with an increased risk of agent-induced toxicity in a patient population. In certain aspects, the PSCs are iPSC cells, optionally created from a patient having a known relevant genotype. In other cases the PSC are human ES cells. Preferably, the cell populations are isogenic cell populations created from genetic modification of an iPSC.

The invention also provides a method of determining risk of agent-induced toxicity in a patient population comprising providing a panel of cell populations produced from differentiated PSCs, wherein the cell populations comprise mutations and/or polymorphisms of the BAG3 chaperone complex, contacting said panel of isogenic cell populations with an agent, and detecting ex vivo activity associated with toxicity resulting from the agent in the cell populations, thereby detecting genotypes of proteins of the BAG3 chaperone complex that are associated with an increased risk of agent-induced toxicity in the patient population.

In preferred aspects, the cell populations used in the present invention are created from induced pluripotent stem cells (iPSCs), and more preferably human iPSCs. The cell populations created using the iPSCs are then further differentiated into cell populations representative of a specific tissue or organ. Such cells populations include, but are not limited to, neurons, muscle cells, hepatocytes, pancreatic cells, retinal cells, and progenitors of each of these cell types.

In other preferred aspects, the cell populations of the invention are created using clonal expansion of a single cell to create an isogenic cell population.

In some aspects, the cell populations of the invention are created by differentiation of human PSCs into cardiomyocytes or cardiomyocyte progenitors. In other aspects of the invention, the cell populations are created by differentiation of human PSCs into peripheral neurons. Preferably the human pluripotent stems cells used for differentiation are isogenic stem cells created from iPSCs In certain aspects, the agent used in the assays and methods of the invention is a proteasome inhibitor. In other aspects, the agent used in the methods of the invention is an agent that modulates autophagy in the cell populations. In specific aspects, the agent is a candidate agent, and the assays of the invention are used to determine the ex vivo activity (and thus predict in vivo activity) of the agent on protein homeostasis in a cell population.

In some embodiments, the assays and methods of the invention use a panel of cell populations having known genotypes of one or more proteins in a chaperone complex. The invention thus further includes panels of cell populations produced from a pluripotent cell source comprising known genotypes of one or more chaperone complex proteins.

In a specific aspect, the panel of cells comprises one or more cell populations with a mutation and/or polymorphism in BAG3. In other aspects, the panel of cells comprises one or more cell populations with a mutation and/or polymorphism in a protein that associates with BAG3 in vivo. Such proteins include, but are not limited to, Hsp70 (HSPA1A), HSPA8 (HSC70), HSPB1 (HSP27), CRYAB (HSPB5), HSPB6, HSPB8, HSPB7, AMOTL1, AMOTL2, FLNC (Filamin C), SQSTM1 (p62), CAPZB, (CapZβ1), YWHAG (14-3-3 complex, subunit gamma), SYNPO2 (Myopodin/synaptopodin 2) PLCG1, (PLC-γ), BCL2, and PDLIM7.

The invention further provides a method for identifying candidate agents that inhibit in vivo toxicity observed in muscle cells exposed to a stressor, comprising the steps of contacting a cell population comprising muscle cells or muscle cell progenitors differentiated from a human pluripotent stem cell line with a candidate agent, exposing the population of cells to a stressor which causes an imbalance of the protein homeostasis in the population of cells, contacting the population of cells with a candidate agent, determining an effect of the candidate agent on the imbalance of the protein homeostasis in the population of cells using a high throughput imaging detection method, and identifying whether the candidate agent improves the balance of protein homeostasis in the population of cells following the exposure of the population of cells to the stressor. A candidate agent that demonstrates an improvement in the protein homeostasis in the cell population ex vivo is thereby identified as an agent for use in inhibition of in vivo toxicity in muscle cells.

The muscle cells or progenitors thereof may be contacted with a candidate agent before or after the cells are exposed to the stressor. In some aspects of this method, the muscle cells are cardiomyocytes or cardiomyocyte progenitors. In other aspects of this method, the muscle cells are skeletal muscle cells or skeletal muscle progenitors. Identification of the effect of the candidate agent is preferably determined using an imaging technique, e.g., to measure sarcomere integrity or to measure beat rate and contractility of the muscle cells.

The invention also provides a method for identifying an increased risk of agent-induced toxicity in an individual comprising performing an assay analyzing whether an individual expresses a chaperone complex protein with a mutation and/or polymorphism that demonstrates an increased risk of cell toxicity in the ex vivo pluripotent stem cell assays of the invention.

The invention further comprises a method for treating a disease in an individual comprising requesting an assay analyzing whether an individual expresses a chaperone complex protein with a mutation and/or polymorphism associated with an increased risk of cell toxicity and administering the agent to the individual if the individual does not express the chaperone complex protein with the analyzed mutation and/or polymorphism. The chaperone complex protein tested for a mutation and/or polymorphism can be BAG3 and/or a protein that associates with BAG3 in vivo. Such proteins include, but are not limited to, Hsp70 (HSPA1A), HSPA8 (HSC70), HSPB1 (HSP27), CRYAB (HSPB5), HSPB6, HSPB8, HSPB7, AMOTL1, AMOTL2, FLNC (Filamin C), SQSTM1 (p62), CAPZB, (CapZβ1), YWHAG (14-3-3 complex, subunit gamma), SYNPO2 (Myopodin/synaptopodin 2) PLCG1, (PLC-γ), BCL2, and PDLIM7.

In some aspects, the disease treated is a form of cancer. In other aspects, the agent is a protease inhibitor. In yet other aspects, the agent inhibits autophagy in a cell.

The present invention also provides panels of cells with genotypic variations in specific proteins and/or protein complexes of multiple chaperone complexes within a patient population. These cells are useful to identify the risk of toxicity in a patient population or individual risk of a patient within the population.

It is an advantage of the present invention that the toxicity seen with an agent in the ex vivo cell-based assays of the invention correlates with in vivo effects of the agent.

It is another advantage of the present invention that the assays can be performed on live cell populations, and thus can measure not only a response to a particular agent, but also the response to a cessation of the agent.

These and other objects, advantages, and features of the invention will become apparent to those persons skilled in the art upon reading the details of the compositions and assays as more fully described below.

DETAILED DESCRIPTION OF THE INVENTION

Figure 1A:
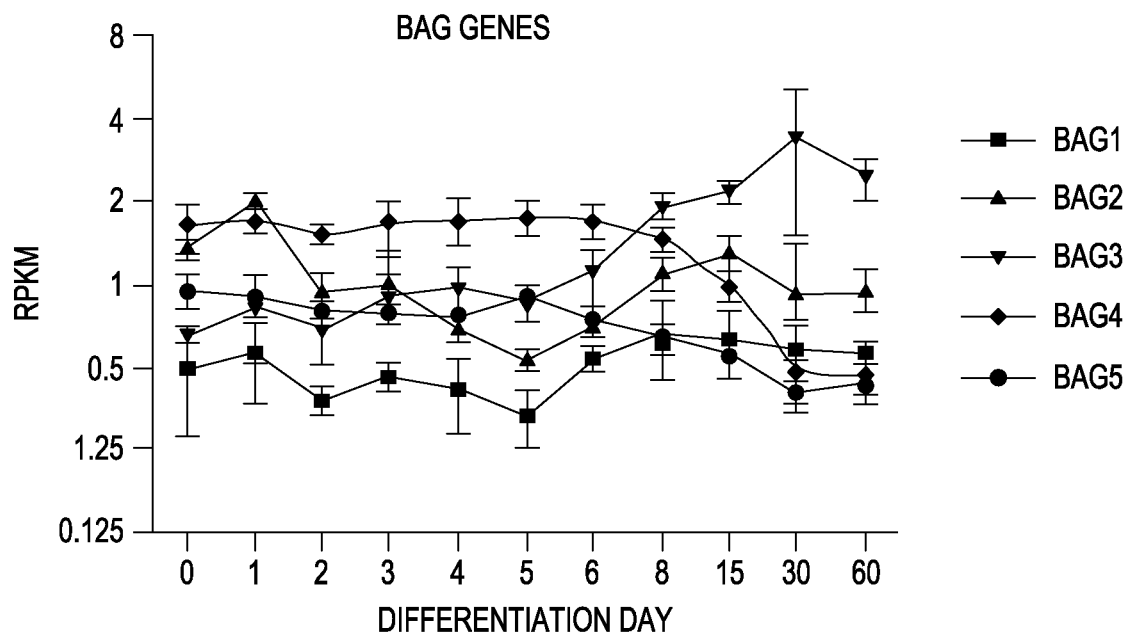
FIGS. 1a and 1b are line graphs showing the difference in expression of BAG genes and HSP genes during differentiation of iPS-CMs from IPSC.

The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular processes and systems provided in particular implementations. However, the processes and systems will operate effectively in other implementations. Phrases such as "exemplary embodiment", "one embodiment" and "another embodiment" may refer to the same or different embodiments.

The exemplary embodiments will be described with respect to methods and compositions having certain components. However, the methods and compositions may include more or less components than those shown, and variations in the arrangement and type of the components may be made without departing from the scope of the invention.

The exemplary embodiments will also be described in the context of methods having certain steps. However, the methods and compositions operate effectively with additional steps and steps in different orders that are not inconsistent with the exemplary embodiments. Thus, the present invention is not intended to be limited to the embodiments shown, but is to be accorded the widest scope consistent with the principles and features described herein and as limited only by appended claims.

It should be noted that as used herein and in the appended claims, the singular forms "a," "and," and "the" include plural referents unless the context clearly dictates otherwise. Thus, for example, reference to the effect of "an agent" refers to the effect of one or a combination of agents, and reference to "a method" includes reference to equivalent steps and processes known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein are incorporated by reference for the purpose of describing and disclosing the formulations and processes that are described in the publication and which might be used in connection with the presently described invention.

Those skilled in the art will recognize, or be able to ascertain using no more than routine experimentation, many equivalents to the specific embodiments of the invention described herein in the detailed description and figures. Such equivalents are intended to be encompassed by the claims.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

"Assay" or "assays" as used in the present invention are intended to describe ex vivo tests performed to measure the effect of an agent on protein homeostasis in a cell, tissue or organ. The effect may be, e.g., on a genetic, protein or functional level.

The term "diagnostic" as used herein refers to any composition or assay of the invention used in order to carry out a diagnostic test or assay on an individual sample. The assays and compositions of the invention may form all or part of a diagnostic test regulated by a federal or state agency. The use of the assays and/or compositions of the invention as a diagnostic tool is intended to be distinct from and unrelated to any use of the composition in the development of therapeutic agents.

The term "increased risk" as used herein, e.g., in the context of risk of agent-induced toxicity, refers to an increase in the likelihood that the contact of a cell and/or individual with an agent will have a statistically higher likelihood of demonstrating a measured effect associated with toxicity than a control cell or individual, e.g. a cell or individual with a wild type genotype in a gene of interest, or a cell or individual that does not display an increase in agent-induced toxicity based on phenotype and/or the assays of the invention. An increased risk may be any greater likelihood that a cell or individual will exhibit the measured effect, but in certain preferred embodiments is at least a 5% greater likelihood that a cell or individual will exhibit the measured effect, more preferably at least a 10% greater likelihood that a cell or individual will exhibit the measured effect, and even more preferably a 20% greater likelihood that a cell or individual will exhibit the measured effect. In specific embodiments, the measured effect associated with toxicity of the agent or condition is 25-100% greater than a control cell or individual, or preferably at least 50-100% greater than a control cell or individual, the latter of which is considered a high risk of agent-induced toxicity.

The term "mutation" as used herein includes any genetic variant in protein sequence, expression, transplantation, transcription, structure and/or function. Such mutations include, but are not limited to single point mutations, triple codon repeats, insertions, deletions, translocations, inversions, rearrangements, and the like.

The term "panel" when used in the context of the cell populations of the invention refers to a collection of at least 2 or more, and preferably 3 or more, and even more preferably 5 or more individual clonal cell populations with distinct genotypes. The distinct genotypes of the cell populations of a panel may be in the same gene or may be within different genes.

The term "patient population" as used herein refers to a subset of individuals that have, are suspected to have, or are being tested for a known mutation and/or polymorphism in a gene of interest.

As used herein, the terms "progenitor" or "progenitor cell type" are any at any stage of differentiation between a pluripotent stem cell and a fully differentiated cell.

The term "stressor" as used herein refers to any environmental stimulus, introduced agent, or other conditions to which a cell may be subjected that results in an imbalance in the proteomic homeostasis of that cell.

The terms "treatment", "treating" and "treat" and the like are used herein to generally mean administering an agent to obtain a desired pharmacological and/or physiological effect. The "treatment" as used herein covers any treatment of a disease in a mammal, particularly a human. The effect may be prophylactic in terms of completely or partially preventing a disease or symptom thereof and/or may be therapeutic in terms of a partial or complete cure for a disease, symptom and/or adverse effect attributable to the disease.

THE INVENTION IN GENERAL

The present invention is based on the development of novel assays for identification of toxicity risk associated with a particular genotype in a patient population and/or an individual within a patient population. The invention is based in part on the ability to direct the differentiation of clonal populations of PSCs such as iPSCs into more mature cells types, and in particular the ability to differentiate populations of PSCs (e.g., isogenic populations) into cell types relevant for determining toxicity. In addition, the high throughput assays described herein utilize detection methods that are reproducible and provide temporal information about the effect of an agent on a particular cell population. Using PSC-derived cell populations reflective of the genotypes of specific proteins within a patient population (e.g., genotypes of the proteins of a chaperone complex) in combination with sensitive, high throughput assays increases the relevance and predictive value of pre-clinical and clinical safety assessment in a cost-effective manner.

The BAG3 chaperone complex is critical in cardiac protein homeostasis and development of dilated cardiomyopathy. New high throughput assays using isogenic cell populations of iPS-CM were developed to demonstrate proof of concept for the wider use of such isogenic cell-based assays involving protein chaperone complexes in diseases associated with a shift in the homeostasis of the integrity of the proteome in a tissue.

In key embodiments, the assays of the invention can detect risk for agent-related toxicity in patient populations where such adverse events are associated with mutations and/or polymorphisms in proteins that are a component of a chaperone complex. In some embodiments, a panel of cell populations with defined human genotypic variations of proteins in a chaperone complex is used. In certain embodiments, the cell populations used in the assay can be created to include one or a multiple of mutations or polymorphisms for a single chaperone complex active in a particular tissue or organ. In another embodiment, the cell populations can be created to include the known mutations or polymorphisms for multiple chaperone complexes active within a particular tissue or organ or within multiple tissues and organs. In still other embodiments, the cell populations may include cells with the same genotype that are differentiated into different cell populations representative of different tissues and/or organs.

In certain aspects, the cell populations used in the invention are created by clonal expansion of a single PSC that has been engineered to have a known mutation and/or polymorphism in one or more alleles of a gene of interest. The generation of these clonal cell populations utilizes a method for introducing a selected mutation and/or polymorphism into a single cell, expanding the cell with the selected mutation and/or polymorphism, and exposing the cell population to differentiation factors to mature the cell to a desired lineage, e.g., cardiomyocytes or cardiomyocyte progenitors. In preferred aspects, methods are used that do not require antibiotic selection or use of other additional genetic selection requiring introduction of sequences not typically found in the human genome. Individual cells with desired mutations and/or polymorphisms are isolated, clonally expanded and differentiated to produce one or more isogenic cell populations for use in the assays and methods of the invention.

In a particular embodiment, the present invention provides a method of providing a panel of isogenic cell populations comprised of varied genotypes of one or more chaperone complex proteins found within a human population. The genotypes preferably include the different mutations and/or polymorphisms that are found within patient populations known or suspected to be at risk of toxicity upon the introduction of an agent. The panel of cells may include cell populations with genotypes for a specific chaperone complex known to be involved in a biological phenomenon or folding of particular client proteins in a desired test tissue, or may be a more general panel which comprises mutations and polymorphisms of multiple chaperone complexes for broader high throughput testing of various tissues using a single clonal panel. Thus, a panel of cells used in the assay of the invention may include cells differentiated into cells of a particular lineage or may include clonal populations with the same genotypes that have been differentiated to reflect various tissue types.

The cell lineages for the assays and methods of the invention include, but are not limited to cardiomyocytes, neurons, skeletal muscle cells, hepatocytes, pancreatic cells, retinal cells, and progenitors of each of these cell types. Preferably, each has an isogenic genotype reflective of a genotype of a gene of interest that may be associated with toxicity within a patient population.

In one embodiment, the present invention provides a panel of pluripotent stem cell-derived cardiomyocytes, and preferably induced pluripotent stem cell-derived cardiomyocytes (iPS-CM), with specific, known mutations and/or polymorphisms representative of a patient population or subpopulation, and assays using such panels of iPS-CM. The ability to differentiate PSCs of known genotype into beating, maturing cardiomyocytes affords a novel path to study cardiovascular biology ex vivo (Trends in Pharmacological Sciences 30: 536-545, 2009). These assays using the panels described in the present invention can accurately detect an increased risk for agent-induced cardiac events in such populations or individuals within such populations based on ex vivo high throughput assays.

In another embodiment, the present invention provides a panel of clonally expanded human neurons or neural progenitors with specific, known mutations and/or polymorphisms representative of a patient population or individuals within that population, and assays using panels of such clonal populations of differentiated cells. These neurons or neural progenitors are preferably differentiated from clonally expanded iPSC. Assays using such panels described in the present invention can accurately detect an increased risk for nerve toxicity (e.g., peripheral nerve toxicity) based on high throughput assays, and preferably ex vivo high throughput assays.

The panels of clonal cell populations described are preferably differentiated from clonally expanded human iPSC.

THE CHAPERONE COMPLEXES

The present invention is in part based upon the premise that a risk of toxicity can be identified in patient populations and/or individuals within such patent populations using assays with panels of isogenic cell populations indicative of different mutations and/or polymorphisms within proteins of the chaperone complexes. It has been shown that inhibition of proteasome activity in certain individuals is associated with a profound cardiac toxicity resulting in death. See, e.g., Bockorny M et al., (2012) *Acta Haematol* 128:244-7. In these individuals, a greater than normal insufficiency in maintaining homoeostasis to maintain proteome stability may lead to proteotoxicity in certain tissues, which is predicted to be at least in part dependent upon the particular chaperone complex. Accordingly, in specific embodiments, panels of differentiated PSCs (e.g., iPSCs) are engineered to have mutations in proteins of one or more members of a chaperone protein complex.

Chaperones assist in the folding of de novo synthesized proteins, the unfolding and refolding of proteins as they traffic into cellular compartments, and in the refolding of proteins when damaged. Mutations in proteins of the chaperone complexes have been implicated in different disorders involving aberrant protein aggregation, including neurodegenerative disorders such as Alzheimer's disease and cardiomyopathy.

In a particular embodiment of the present invention, the cell populations used in the assay are cardiomyocytes or progenitors thereof created to mimic the genetic variability of individuals with an adverse reaction to proteasome inhibitors. Inhibition of proteasome activity in certain individuals has been associated with serious adverse events, including death, upon administration of proteasome inhibitors. See, e.g., Bockorny M et al., (2012) *Acta Haematol* 128:244-7.

The present invention provides proof of concept for detecting a risk of toxicity associated with a chaperone complex active in cardiomyocytes. The invention, however, is intended to cover the use of cell populations with mutations and/or polymorphisms in other chaperone complexes found in different tissues, and the described methods are equally applicable to cell populations having mutations and/or polymorphisms in chaperone complex proteins active in different tissues, disease states, and responsive to other agents or candidate agents. The following are exemplary molecules involved in the homeostasis of the proteome in different cell types and physiological processes dependent upon the activity of the chaperone complexes, and the invention is thus intended to include, but is not limited to, assays utilizing cells having specific genotypes of the various proteins as discussed below.

Heat shock protein 70 (Hsp70) belongs to an abundant family of molecular chaperones that regulates protein quality control (i.e. homeostasis) within cells (Finka A and Goloubinoff P (2013) *Cell Stress Chaperones* 18, 591-605). Members of this family are thought to play key roles in virtually every cellular process that involves proteins, including folding, stabilization, trafficking, and turnover. Hsp70 is a 70-kDa protein that consists of two domains: an N-terminal nucleotide binding domain (NBD) responsible for binding and hydrolyzing ATP and a C-terminal substrate-binding domain (SBD) that binds to "client" proteins. The clients of Hsp70 include a wide range of unfolded, misfolded, and partially folded proteins.

Hsp90 is one of the most abundant cellular chaperone proteins. It functions in a multi-component complex of chaperone proteins that may include p60/Hop, p50Cdc37, Hsp40/HDJ2, p23, Hsp70 and one of a variety immunophilins (Young J C et al. (2001) *J Cell Biol* 154: 267-273; Pratt W B and Toft D O. (1997) *Endocr Rev* 18: 306-360. It accounts for 1-2% of total protein in unstressed cells and increases to 4-6% of cellular proteins under stress. (Goetz M P et al., (2003) *Annals of Oncology* 14: 1169-1176). Unlike other chaperones, Hsp90 distinguishes itself in that most of its known clients are protein kinases or transcription factors involved in signal transduction (Richter K and Buchner J (2001). *J Cell Physiol;* 188: 281-290. Hsp90, in particular, has been characterized as the driver for Hsp-mediated proteasomal degradation (Mimnaugh, E et al. (1996) *J. Biol. Chem.* 271, 22796-22801; Neckers, L et al., (1999) *Invest. New Agents* 17, 361-373).

Cochaperones, including the J proteins and the nucleotide exchange factors (NEFs), interact with Hsp70 and guide its various activities. Specifically, the J proteins are a family of cochaperones that bind to Hsp70 in a region between the NBD and SBD (Ahmad A. et al., (2011) *Proc. Natl. Acad. Sci. U.S.A.* 108, 18966-18971. This interaction stimulates ATP hydrolysis and promotes client binding (Laufen T et al., (1999) *Proc. Natl. Acad. Sci. U.S.A.* 96, 5452-5457). In addition, some J proteins interact with clients directly. Thus, they are believed to recruit proteins to the Hsp70 system (Kampinga H. H. and Craig E. A. (2010) *Nat. Rev. Mol. Cell Biol.* 11, 579-592).

Conversely, the NEFs are cochaperones that bind the NBD of Hsp70 to accelerate ADP and client release. Some of the NEFs act as scaffolding proteins, linking Hsp70 and its clients to a variety of cellular pathways (Bukau B. et al., (2006) *Cell* 125, 443-451). Thus, the cochaperones of Hsp70 are thought to modify the enzymatic activity of the chaperone and help guide its interactions with protein clients and other cellular factors.

Proteins with Bcl2-associated anthanogene (BAG) domains act as nucleotide exchange factors for Hsp70. These proteins have been identified on the basis of an~100-amino acid BAG domain. There are six BAG family members in humans, and each is thought to link Hsp70 to a distinct cellular pathway. The BAG domain is thought to promote nucleotide release by binding to the nucleotide binding domain of Hsp70. In addition to their shared BAG domain, the members of the BAG family have additional domains with specialized functions (Doong H. et al. (2002) *Cancer Lett.* 188, 25-32). The specificity of which BAG protein is bound to Hsp70 appears to help determine what will happen to the Hsp70-bound client. The interaction between Hsp70 and these cochaperones is thus critical to provide homeostasis and stability to the proteome.

BAG1, for example, has an ubiquitin-like (UBL) domain that targets Hsp70 clients to the proteasome (Lüders J. et al. (2000) *J. Biol. Chem.* 275, 4613-4617; Tsukahara F. and Maru Y. (2010) *Blood* 116, 3582-3592; Alberti S. et al. (2003) *Cell Stress Chaperones* 8, 225-231). BAG1 also binds to the antiapoptotic kinase Raft, and it works with Hsp70 to stabilize that protein in cancer (Song J. et al., (2001) *Nat. Cell Biol.* 3, 276-282). Conversely, BAG2 has been associated with promoting the degradation of large aggregates, such as phosphorylated Tau (Carrettiero D. C. et al. (2009) *J. Neurosci.* 29, 2151-2161). BAG3 has multiple protein-protein interaction motifs that link the Hsp70-BAG3 complex to the small heat shock proteins Hsp20 and Hsp22, the signaling molecule PLC-γ, 14-3-3 proteins, and the autophagy pathway (Gamerdinger M. et al. (2009) *EMBO J.* 28, 889-901; Xu Z. et al. (2013) *J. Cell Sci.* 126, 4173-4186; Carra S., et al., (2008) *J. Biol. Chem.* 283, 1437-1444; Doong H. et al. (2000) *Oncogene* 19, 4385-4395).

BAG3 also serves as a scaffold that binds and coordinates small heat shock proteins (sHSPs) and Hsp70 proteins in cardiac and neuronal tissues (See, e.g., Rauch J N and Gestwicki J E. (2014) *J Biol Chem* 289:1402-14. Hsp70 (HSPA1A), HSPA8 (HSC70), HSPB1 (HSP27), CRYAB (HSPB5), HSPB6, HSPB8, HSPB7, AMOTL1, AMOTL2, FLNC (Filamin C), SQSTM1 (p62), CAPZB, (CapZβ1), YWHAG (14-3-3 complex, subunit gamma), SYNPO2 (Myopodin/synaptopodin 2) PLCG1, (PLC-γ), BCL2, and PDLIM7.

The BAG3 complex orchestrates protein folding, proteasomal degradation, and autophagy—all critical steps in ensuring protein homeostasis within cells. Specific mutations in the BAG3 gene cause strikingly different clinical phenotypes, suggesting that those mutations could have dominant-negative effects linked to distinct cellular pathways and disease phenotypes, including muscular dystrophy, giant axonal neuropathy (Jaffer F et al., (2012) *J Peripher Nery Syst* 17:210-6), myofibrillar myopathy (Odgerel Z et al., (2010) *Neuromuscul Disord* 20:438-42), and dilated cardiomyopathy (Franaszczyk M et al., (2014) *J Transl Med* 12:192).

Hexameric chaperone rings, whose barrels are composed of AAA+ ATPase modules, are involved with ATP-mediated unfolding of proteins in such contexts as protein degradation, protein disassembly, and protein trafficking across membranes (Sauer et al., (2004) *Cell* 119, 9-18). For example, in preparation for proteasomal degradation, a hexameric ring of AAA+ ATPases at the base of the 19S particle of the proteasome unfolds proteins and translocates them into the cylindrical 20S protease core. And in trafficking, p97 pulls on proteins during retrotranslocation from the ER as one of its several actions, whereas the N-ethylmaleimide-sensitive factor (NSF) assembly pulls apart helical-bundle SNARE complexes to enable SNARE components to participate in vesicle fusion. (Bukau B. et al., (2006) *Cell* 125, 443-451).

Cell populations having mutations and/or polymorphisms in these and other proteins involved in chaperone complexes are intended to be covered by the present invention.

ASSAY SYSTEMS OF THE PRESENT INVENTION

The present invention provides assay systems utilizing a novel combination of PSC-derived cell populations and functional read outs to identify the presence and/or level of protein homeostasis imbalance in cell populations. The assay systems using these elements are particularly well suited for predicting in vivo activities of various agents, including candidate agents, that affect such tightly controlled systems in various cell types and/or patient populations. Importantly, the agents can be tested using levels that are similar to the dosage levels used for treatment in individuals, and can therefore be used to demonstrate predictive toxicity of the cells at such clinically used levels.

In one embodiment, the isogenic cell populations of the invention can be used to determine the likelihood that a particular agent will cause toxicity in an individual or patient population with a particular genotype in a gene of interest. In many instances, a panel of cells can be used to provide a method of high throughput screening of various agents or candidate agents to identify a risk of toxicity for individuals with a particular genotype. For example iPSC-derived cells engineered to have specific mutations and/or polymorphisms in proteins of one or more chaperone complexes can be used to identify the risk that a particular agent will cause a detrimental shift in the homeostasis of protein folding in a particular tissue, and thus identify the risk of proteotoxicity arising from such an imbalance within the cells. Such differentiated iPSC-derived cells may be exposed ex vivo to an agent to be tested, and then assayed for their phenotypic response to the agent as described herein.

The response of the iPSC-derived cells to the agent may be compared to a reference response obtained in control iPSC-derived cells, e.g., cells with a genotype of one or more individuals who do not display toxicity for a particular agent or who have a known genotype consistent with a low risk of toxicity in response to the agent tested. The assay can identify an increased risk of agent-induced toxicity in an individual with a specific genotype in a gene of interest, which in turn may identify a patient population that may be at risk for increased agent-induced toxicity.

The assays and cell populations of the present invention are useful to assist in determining the clinical course of treatment in individuals by identifying individuals at an increased risk of toxicity following administration of an agent. For example, where the subject is suffering from a health condition, and multiple agents are available to treat the health condition, the efficacies and adverse effects of the multiple agents may be evaluated using iPSC-derived cell populations corresponding to the genotype of that individual. This information can be a valuable tool in determining the best clinical course of treatment by a health care provider.

In other embodiments, the invention provides an assay method for detecting candidate agents that may improve the disruption of homeostasis in muscle cells (e.g., cardiomyocytes, skeletal muscle cells and/or progenitors thereof). The assays of the invention utilize detection techniques that allow the screening process to be very high-throughput while providing functional information on the candidate agent that improves the chances it will be active in vivo as compared to agents identified in conventional biochemical screening systems. The assays include the steps of contacting a first ex vivo population of muscle cells, and preferably muscle cells differentiated from human iPSCs, with a candidate agent, exposing the muscle cells to stressor associated with an imbalance of the protein homeostasis in the muscle cells, and determining an effect of the candidate agent on the imbalance of the protein homeostasis in the muscle cells using a high throughput detection method. The high throughput method can identify whether or not the candidate agent improves protein homeostasis in the muscle cells, thereby providing a functional read out on the activity of the candidate agent. A candidate agent that improves the balance of protein homeostasis in the muscle cells can be predictive of an agent that has a reasonable likelihood of ameliorating toxicity resulting from an imbalance of cellular protein homeostasis in vivo. Thus, the methods provide an assay for identifying agents that improve protein homeostasis in muscle cells that is both high throughput and high content.

Preferably, the activity of an agent or candidate agent is determined using a live cell imaging assay. Live cell imaging allows a tracking of the effect of an agent or candidate agent in a cell population (or even individual cells) before, during and/or after administration of the agent or candidate agent, allowing not only the ability to identify the effect of administration of an agent over time but also the effect if administration of an agent is discontinued. Thus, live cell imaging is able to capture the temporal nature of the effect of any agent on a treated cell population, in contrast to assays with end points that require lysis or fixing of the cells. Live cell imaging assays also reduce assay-to-assay variability, as the systems can be automated.

In one aspect, the assay systems of the invention utilize imaging to determine beat rate, beat intensity and/or contractility of cardiomyocytes as the functional read out of the high throughput assay of the invention. Beat rate and beat intensity of cardiomyocytes or cardiomyocyte progenitors can be measured using methods such as video microscopy and image analysis. A preferred method generates automated measurements of beating frequency, beat duration, amplitude, and beat-to-beat variation based on motion analysis of phase-contrast images captured at a fast frame rate. See, e.g., Maddah M et al., (2015) *Stem Cell Reports* 4:621-31. Spontaneous beating can be measured using optical mapping motion detection software (Maddah, id; Huebsch N et al. (2015) *Tissue Eng Part C Methods* 21:467-79. These measurements can be performed on live cells, and imaging carried out over a period of time.

In alternative aspects, the assays of the invention utilize imaging to determine sarcomere alignment and integrity in muscle cells as the functional read out of the high throughput assay of the invention. The imaging of sarcomere integrity can be used to calculate an efficacy/toxicity index, and such index in turn may be useful for decision making on whether or not to proceed with the development of a candidate compound and/or for re-defining the development criteria for a potential successor compound.

Figure 3:
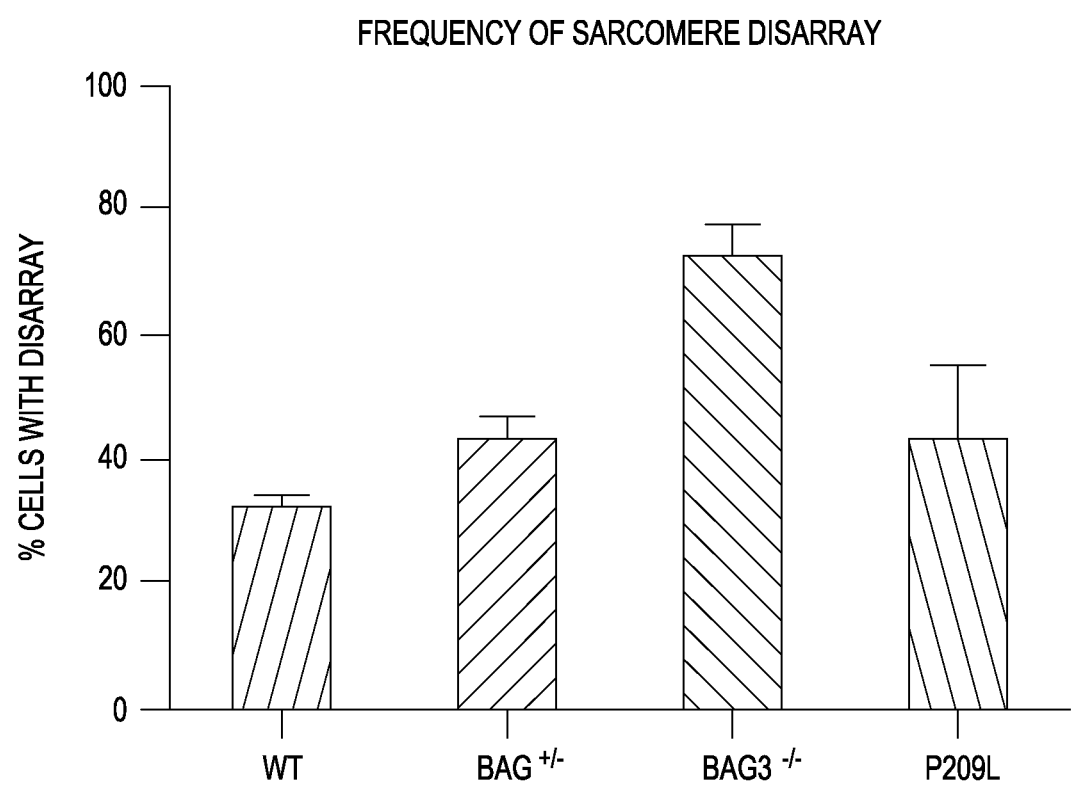
FIG. 3 is a bar graph showing the quantification of sarcomeric disarray of BAG3 mutant iPS-CMs as compared to WT iPS-CMs.

In one preferred exemplary method, live cells are imaged using reporter molecules used to identify sarcomeres, and these images observed over time. The advantage of the live cell imaging process is that it can be repeated over many cycles, and the alterations of the sarcomere alignment can be tracked before and through the exposure to a stressor and/or contact with the candidate agent. Repetitive imaging can be used for computer-aided scoring in live cells, and compared to reference cell populations or to multiple cell populations tested in the same or comparable conditions. This read out also allows a tracking of sarcomere integrity and organization before, during and/or after administration of the agent to allow identification of the effect of an agent as well as any effect when administration of an agent is discontinued. The results of one example of such a high throughput detection method using detection of sarcomere disarray is shown in FIG. 3.

An additional exemplary method for visualizing sarcomere alignment and integrity is fixed cell sarcomere analysis, in which fixed cells are stained for a cell-specific protein (such as actinin) and imaged to determine the extent of sarcomeric disarray. This imaging can be aided, e.g., by computer based algorithms to compare levels of staining in particular cell populations.

Other assay end points may also be used to assess the effect of compounds in the assays of the present invention. These include, but are not limited to: autophagy assays, such as the LC3 autophagy assay (Barmada S J et al., *Nat Chem Biol* 10:677-85; Murrow L and Debnath J. (2013) *Annu Rev Pathol* 8:105-37) or assays using proteins such as proteasome inhibitors to measure autophagy flux; aggregation assays, which utilize cell disruption and detection of insoluble fraction to determine the extent of aggregation in the cell (Ulbricht A et al. (2013) *Curr Biol* 23:430-5); protein quality control assays, in which likely client proteins are tagged, e.g., a with photo-convertible agent (Paez-Segala M G et al. (2015) *Nat Methods* 12:215-8), and optical pulse-labeling used to determine the flux of the protein as a measure of protein quality control and aggregation (Barmada S J et al., *Nat Chem Biol* 10:677-85); electrophysiology assays such as patch clamp measurement and sharp electrode patching; and tissue physiology assays including use of tissue and microtissue models, which can be mounted on force transducers and paced to directly measure force generation.

DIFFERENTIATION OF PSCS FOR USE IN THE ARRAYS OF THE INVENTION

The PSCs cells created for use in the present invention can be differentiated into various cell types of interest that may be of clinical use for determination of the risk of toxicity from administration of an agent. The following are exemplary methods for the differentiation of various cells, and is not meant to be a limiting or exhaustive list.

Methods of differentiating pluripotent stem cells into cardiomyocytes are disclosed, for example, in U.S. App. No. 20150125952, U.S. App. No. 20140363841, U.S. App. No. 20140314725, U.S. App. No. 20140220555, U.S. App. No. 20140134733, U.S. App. No. 20140094388, U.S. App. No. 20140087460, U.S. App. No. 20130230921, U.S. App. No. 20130224857, U.S. App. No. 20130189785, U.S. App. No. 20130177535, U.S. App. No. 20130157947, U.S. App. No. 20130011371, U.S. App. No. 20130011371, and U.S. App. No. 20110136681.

Methods of differentiating pluripotent stem cells into neural cells are disclosed, for example, in U.S. App. No. 20150159133, U.S. App. No. 20150093761, U.S. App. No. 20150038371, U.S. App. No. 20150093761, U.S. App. No. 20150004701, U.S. App. No. 20140248696, U.S. App. No. 20140065227, U.S. App. No. 20130280804, U.S. App. No. 20130224857, U.S. App. No. 20130177535, U.S. App. No. 20130157947, U.S. App. No. 20130059309, U.S. App. No. 20110136681.

Methods of differentiating pluripotent stem cells into hepatocytes are disclosed, for example, in U.S. App. No. 20140134143, U.S. App. No. 20130259836, U.S. App. No. 20130251694 U.S. App. No. 20130224857, U.S. App. No. 20130217752 U.S. App. No. 20130177535, U.S. App. No. 20130130374, U.S. App. No. 20130157947, U.S. App. No. 20120190059 and U.S. App. No. 20110136681.

Methods of differentiating pluripotent stem cells into skeletal muscle cells are disclosed, for example, in U.S. App. No. 20150125952, U.S. App. No. 20150159140, U.S. App. No. 20130224857 and U.S. App. No. 20130224857.

Methods of differentiating pluripotent stem cells into pancreatic cells are disclosed, for example, in U.S. App. No.

20150159140, U.S. App. No. 20150157668, U.S. App. No. 20150104430, U.S. App. No. 20140329315, U.S. App. No. 20140242693, U.S. App. No. 20140234963, U.S. App. No. 20130210060, U.S. App. No. 20120264209, U.S. App. No. 20120264209, and U.S. App. No. 20130177535.

Methods of differentiating pluripotent stem cells into retinal epithelial cells or retinal progenitor cells are disclosed, for example, in U.S. App. No. 20150159134, U.S. App. No. 20120204282, U.S. App. No. 20110081719 and U.S. App. No. 20110002897.

Panels of the above described cells can be produced using, e.g., U.S. App. No. 20130045892.

CLINICAL TRIAL DESIGN AND RISK STRATIFICATION

The cell populations of the invention may be particularly useful in clinical trial design. The assays of the invention allow identification of individual patient populations that exhibit varied responses to agents, aiding in the optimization of the inclusion and exclusion criteria key to a successful trial design. These assays also provide insight into the mechanisms of agent-induced toxicity, and provide an attractive alternative to the current reliance on live animal testing for determining toxicity of drugs in development. In addition, the use of human cells may identify species-specific toxicities that are not identified using non-human models. Such predictive toxicity assays can help calibrate the potential safety issues of promising agent candidates early in the development process, preventing attrition later in drug development. Importantly, the present assays can identify patient populations that may be particularly at risk of serious adverse events based on genotype, and prevent toxicity and even death in certain individuals. This will allow development of drugs with potentially great benefit to certain populations to progress, while reducing the risk of toxic effects to other patient populations.

REDUCTION OF TOXICITY RISK FOR THERAPEUTIC ADMINISTRATION OF AGENTS

The present invention also provides a test for identifying an individual at risk for cellular toxicity following the administration of particular agents, e.g., proteasome inhibitors. The test utilizes the novel ability of the assays of the invention to identify particular polymorphisms and/or mutations in proteins of the chaperone complex of an individual that lead to an increased risk of toxicity upon the inhibition of proteasome activity or autophagy. Individuals with a genotype that demonstrate cell-based toxicity in the chaperone protein assays of the present invention can be identified as being at high risk of agent-induced toxicity prior to the administration of the agent to the individual. Thus, based on identification of a genotype in an ex vivo assay, the potentially lethal consequences of administration of an agent that inhibits proteasome activity or autophagy in an individual can be prevented. In addition, this assay may be used to modify the inclusion/exclusion criteria of a therapeutic agent in development, and to assist in selecting a population for clinical trials that will likely benefit from the agent but which will not exhibit serious adverse events that may preclude regulatory approval of the agent.

Accordingly, the present invention provides a method, including a diagnostic method, for performing an assay to analyze whether an individual expresses a chaperone complex protein with a mutation and/or polymorphism that demonstrates an increased risk of cell toxicity in an ex vivo chaperone complex protein assay of the invention.

In addition, health care providers will benefit from using the methods and assays of the invention as a companion to determining a course of therapy for a particular individual, and in particular when treatment may include therapeutic intervention utilizing agents which inhibit proteasome activity or autophagy. Information on potential toxicity of an agent can be critical in preventing serious adverse events in patients. To prevent the potentially detrimental effects of such agents, health care providers can request an assay be performed to analyze whether an individual expresses a chaperone complex protein with a mutation and/or polymorphism associated with an increased risk of cell toxicity resulting from administration of an agent that inhibits proteasome activity or autophagy. The health care provider can then utilize this information in determining whether an individual would benefit from the administration of this agent, or whether the individual is at high risk for cell-based toxicity and therefore is not a viable candidate for therapeutic intervention by administration of the agent. Thus, if an individual does not express the chaperone complex protein with the analyzed mutation and/or polymorphism, the health care provider can proceed with a course of therapy comprising administration of the agent.

The use of the methods of the invention in therapeutic decisions is important, for example, in determining the use of various agents in oncology. Proteosome inhibitors such as the approved drug bortezomib have been shown to have lethal toxicity in a small but significant patient population. Mutations in the BAG3 chaperone complex have been associated with such toxicity based on ex vivo studies which correlate with known genotypes in the patient population. Thus the result of an assay to determine whether an individual has a mutation in BAG3 or in a protein known to associate with BAG3 in vivo would provide valuable information to a health care provider in determining whether a proteasome inhibitor such as bortezomib or carfilzomib should be used in that individual patient.

EXAMPLES

The following examples are put forth so as to provide those of ordinary skill in the art with a complete disclosure and description of how to make and use the present invention, and are not intended to limit the scope of what the inventors regard as their invention, nor are the examples intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Figure 1B:
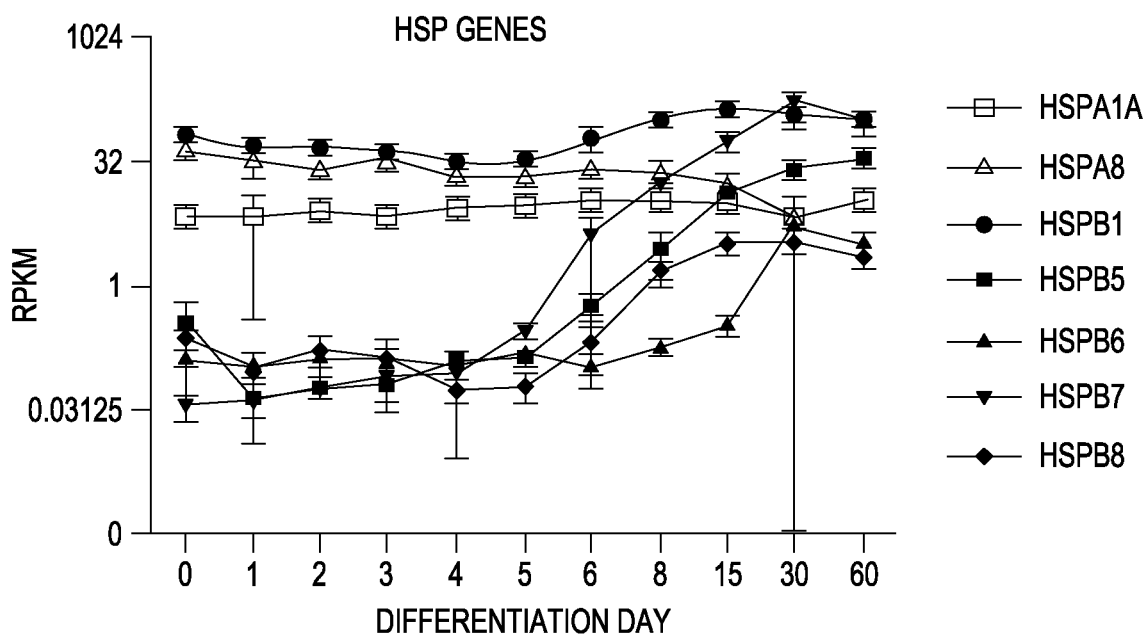

Example 1: Induction of a Cardiac Specific Chaperone Program During Directed Differentiation of Human Induced Pluripotent Stem Cells Transcriptome profiling by RNA-seq during directed differentiation of human induced pluripotent stem cells (iPSC)

into cardiomyocytes (iPS-CM) demonstrated the induction of a cardiac specific chaperone program, including increased expression of BAG3 and HSPB5-8 (FIGS. 1a-1b).

Control iPS cells were differentiated into cardiomyocytes using the protocol described in US Pat App. 20130189785 (See also Lian et al (2012) *Nat Protoc.* 2013 January; 8(1):162-75) and total RNA was extracted at the time points shown up to 60 days after the start of differentiation. Normalized reads per kilobase per million reads (RPKM) were plotted for each gene over the course of differentiation, as means of analyzing triplicate samples with standard deviation. Inducible Hsp70 and constitutive Hsc70 are encoded by HSPA1A, HSPA8 respectively. Small heat shock proteins are encoded by HSPB genes, and CRYAB is also known as HSPB5.

The BAG3 protein was detectable at low levels in the cytoplasm of undifferentiated human iPSC but increased significantly (approximately 10-fold) in iPS-CM, where it was enriched at the sarcomeric Z-disk and the perinuclear region.

Example 2: Generation of Isogenic Cell Populations with Mutations in BAG3

A series of individual isogenic cell populations having mutations in the endogenous human BAG3 locus were made in a reference iPSC line derived from a male volunteer who had a normal electrocardiogram and no family history of heart disease. These mutations included a heterozygous knockout in the BAG3 locus, a homozygous knockout of the BAG3 locus, and a P209L point mutation in the BAG3 locus. BAG3 mutant lines were created using independent strategies including a traditional knockout vector, rare allele induction and detection (RAID), Cas9 genomic editing, and/or TALEN induced targeting vectors. Different targeted nucleases were designed to introduce these mutations. The iPSC KO of BAG3 provides a valuable null background to demonstrate the phenotype in a complete BAG3$^{-/-}$ line.

Having multiple independent BAG3 knock out cell populations created through different methods minimizes the chance that the phenotype results observed using these BAG3 KO cells would be due to off-target effects. These cell populations were produced in both heterozygous and homozygous forms.

The first BAG3 KO cell population was created by introducing a nonsense mutation and a positive selection cassette in the second exon. Briefly, BAG3 KO lines were generated using TALEN-induced targeted integration of the knockout vector in exon 2. Vector included flanking homology arms with a terminator sequence in three reading frames followed by mCherry fluorescent protein and puromycin selection cassette (P$^r$) driven by EF1α promoter.

Figure 2:
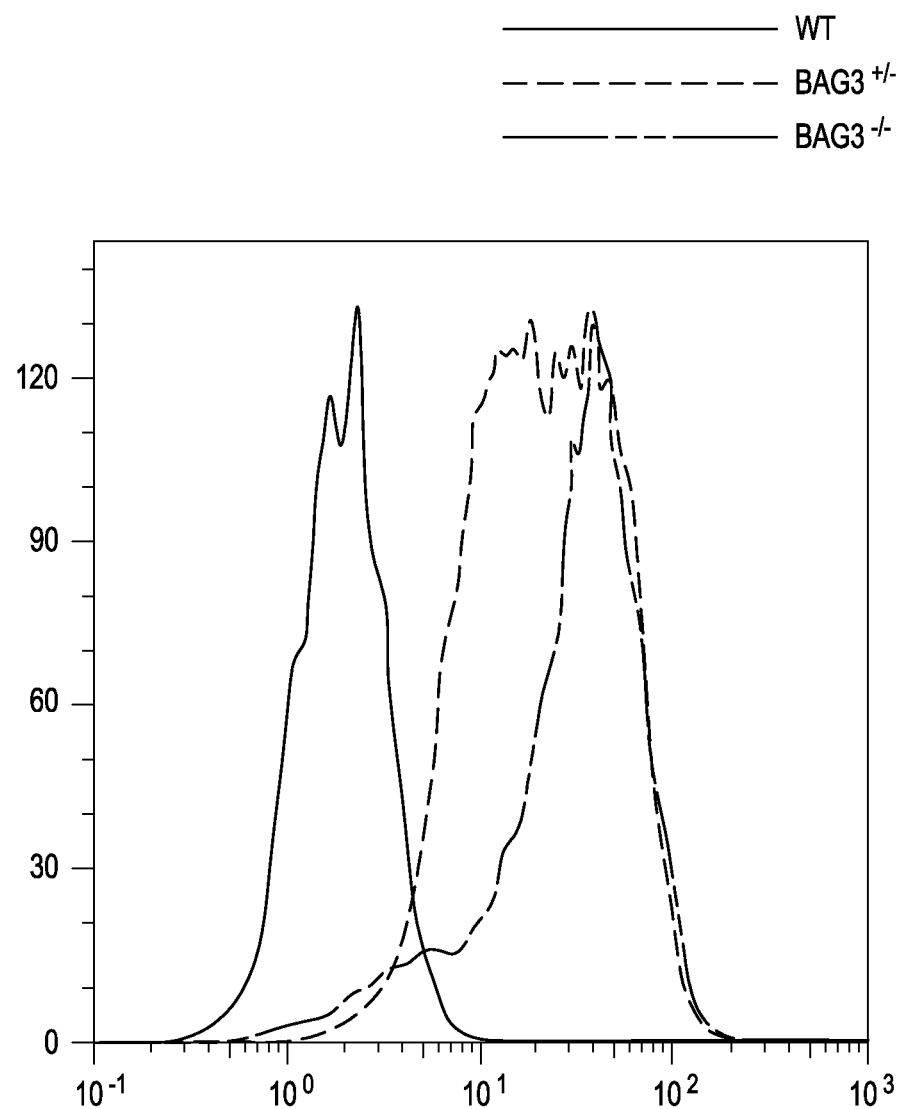
FIG. 2 is a histogram showing the level of BAG3 protein detected in isogenic BAG3 heterozygous and homozygous KO iPS-CM populations as compared to WT iPS-CM populations.

A separate population of BAG3 knock out cell lines was created by the introduction of an early stop codon in the second exon of BAG3 near position 151 of the protein, without the use of a selection cassette. Transient expression of Cas9 with a guide RNA targeted downstream in exon 2 induced small insertions/deletions by non-homologous end joining. Frameshifts caused by indels resulted in early nonsense mutations. These cell lines were tested by flow cytometry to measure BAG3 protein levels using an antibody to BAG3. These experiments demonstrated lack of BAG3 in iPS-CM with homozygous frameshift mutation, with variably reduced BAG3 levels in iPS-CM with heterozygous frameshift mutation (FIG. 2)

Multiple naturally occurring mutations in BAG3 result in premature stop codons in BAG3, which presumably result in loss of BAG3 protein through mRNA nonsense-mediated decay. Western blots confirmed that there is a decrease in the amount of BAG3 protein in BAG3$^{-/+}$ iPS-CMs and no production of BAG3 protein in BAG3$^{-/-}$ iPS-CMs.

Since BAG3 has over 50 reported naturally occurring mutations, multiple criteria were used to choose the isogenic point mutations in iPSCs to maximize their scientific value. The key disease-causing mutations that were selected for further study are located in the binding domains for these chaperone partners. For example, the P209L mutation was chosen because it has the sequence of one IPV domain, which mediates the sHSP interaction. The E455K mutation was chosen because it elicits a severe clinical phenotype and, as shown biochemically, it disrupts the Hsp70 interaction. Rauch J N and Gestwicki J E. (2014) *J Biol Chem* 289:1402-14; Homma S et al. (2006) *Am J Pathol* 169:761-73. This mutation maps to a critical part of the predicted 3D crystal structure of the BAG domain-Hsp70 interface. Arakawa A et al. (2010) *Structure* 18:309-19. The BAG3 mutations were engineered into the iPSC line in both heterozygous and homozygous form. On the basis of the individual phenotypes, and the effects seen in the BAG3 heterozygous and homozygous knock out cells, severe ex vivo phenotypes were expected in the clonal cell populations having these BAG3 mutations (e.g., P209L and E455K).

RAID combines efficient mutation detection, sib-selection (McCormick M. (1987) *Methods Enzymol* 151:445-9) and isolation of rare, scarless clones with the desired mutation. Droplet digital PCR was used for this purpose (Hindson B J et al. (2011) *Anal Chem* 83:8604-10) and the growth conditions of iPSCs were adapted so that rare mutant clones could be isolated with unprecedented efficiency. Unlike traditional methods to generate mutant cell lines that use antibiotic resistance markers, which leave a genetic "scar" that can interfere with splicing or regulation of the endogenous gene, the RAID method used new site-specific nucleases to create scarless, single-base genome editing. The methods used to perform mutagenesis also allowed isolation of these very rare mutant cells from their neighbors without fluorescence or antibiotic selection. Cloning was only attempted after the mutation had been detected, so no effort was expended to isolate and screen large numbers of unmodified iPSC clones. Three independent clonal cell populations were made for each of the individual BAG3 mutations.

Alternatively, point mutations were introduced into the isogenic cardiomyocyte populations using transcriptional activator-like effector nucleases (TALENs) or Cas9-directed gene editing. Isogenic cell populations with the missense mutation P209L were also generated by transient expression of TALENs and single stranded oligonucleotide donor containing the mutation.

Example 3: Sarcomeric Disarray in Untreated Isogenic BAG3 Mutant Cell Populations BAG3$^{-/-}$ cells differentiate into functional iPS-CMs, but display a clear phenotype of sarcomeric disarray in fixed cells. BAG3$^{-/-}$ iPS-CMs show prominent sarcomeric disarray after cellular stress. BAG3$^{-/-}$ iPS-CMs were exposed to cellular stress by either replating or undergoing a freeze-thaw cycle, allowed to recover for 1 week, fixed, and stained for sarcomeric α-actinin. The degree of sarcomeric disarray was scored in a blinded fashion. **p<0.01 vs. WT. Quantification of sarcomeric disarray showed significant difference between all BAG3 mutant lines compared to WT in multiple experiments. (FIG. 3) Disarray was defined by percentage of cells scored as class 3-5, * p<0.05 compared to WT via t-test.

The iPS-CM were also plated on glass surface were fixed and stained with antibodies to BAG3 and sarcomeric α-actinin (ACTN2) to label Z-disks. BAG3-/- cells frequently displayed fragmentation of myofibrils and disintegration of Z-disk structures that were replaced by disordered aggregates (data not shown).

For labeling of sarcomeres in live cells, an alpha-actinin2 cDNA was generated with C-terminal fusion of a V5 epitope tag and mKate2 fluorophore. The construct actinin-mKate was introduced by transient plasmid transfection directly into cardiomyocytes. Labeled cardiomyocytes with wild type, BAG3+/- and BAG3-/- genetic backgrounds were generated from this method. Cardiomyocytes were generated and cryopreserved as described above. Cryopreserved cardiomyocytes were thawed and replated into 48-well plates after transfection, as described above. Images of individual cells were obtained using 40× objective on a Zeiss Z1 microscope with automated stage and ZEN Digital Imaging for Light Microscopy (Zeiss International, Germany). The coordinates of each region of interest were recorded to allow serial imaging of the same cells over time. Cells were treated with vehicle or drug as described above and images were obtained for each recorded region of interest every 24 hours.

Example 4: Effect of Proteosome Inhibitors on Beat Rate of IPS-CM Populations

The effect of proteasome inhibitors bortezomib and carfilzomib on the beat rate of iPS-CM populations were then tested on wild-type, BAG3$^{+/-}$ and BAG3$^{-/-}$ iPS-CMs.

Figure 4:
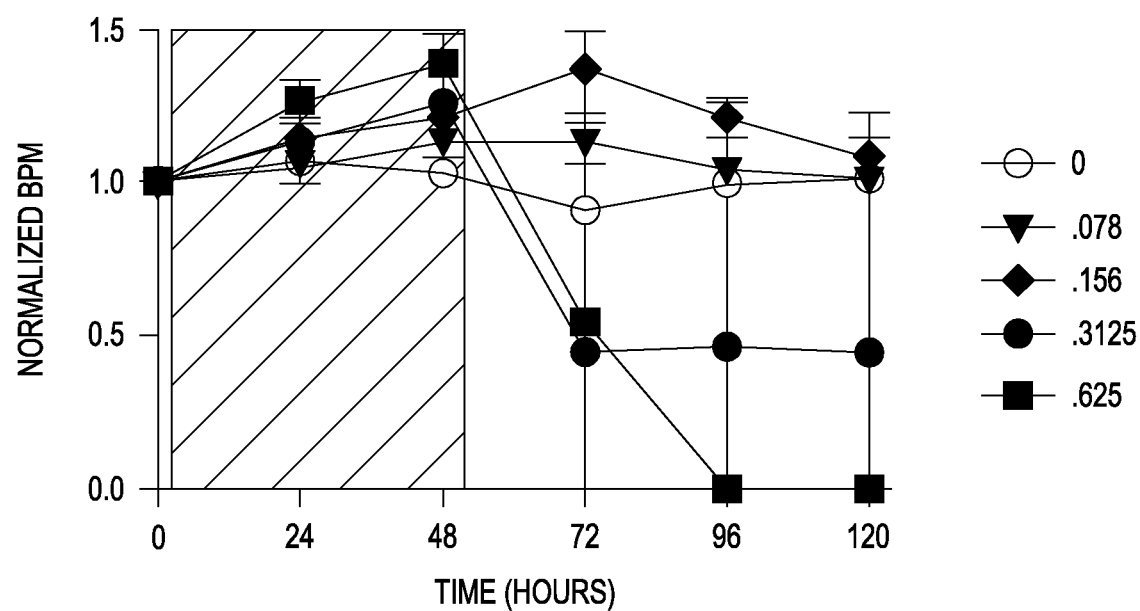
FIG. 4 is a line graph showing the effect of varying doses of proteasome inhibitor bortezomib on beat rate of wild type iPS-CMs.
Figure 5:
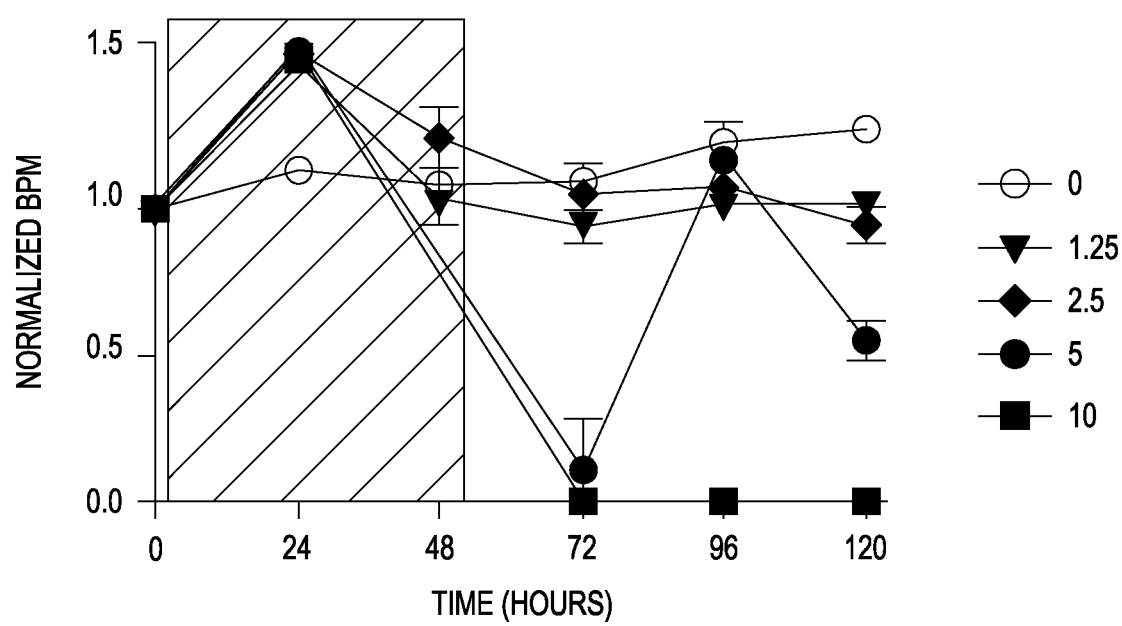
FIG. 5 is a line graph showing the effect of varying doses of proteasome inhibitor carfilzomib on beat rate of wild type iPS-CMs.

Beat rate in wild-type iPS-CM was measured before and after varying doses of bortezomib or carfilzomib. Measurements were obtained every 24 hours for 5 days, with cells exposed to drug for the first 48 hours. Shown are mean and standard deviation of replicate wells. Drug concentrations are in micromolar. Both proteasome inhibitors produced a transient increase on wild-type iPS-CM beat rate. Bortezomib (FIG. 4) required lower doses than carfilzomib (FIG. 5) to achieve similar effects, but this is also consistent with the drug dosages used in humans. The effects of both drugs were reversible at lower doses in the WT iPS-CM.

Figure 6:
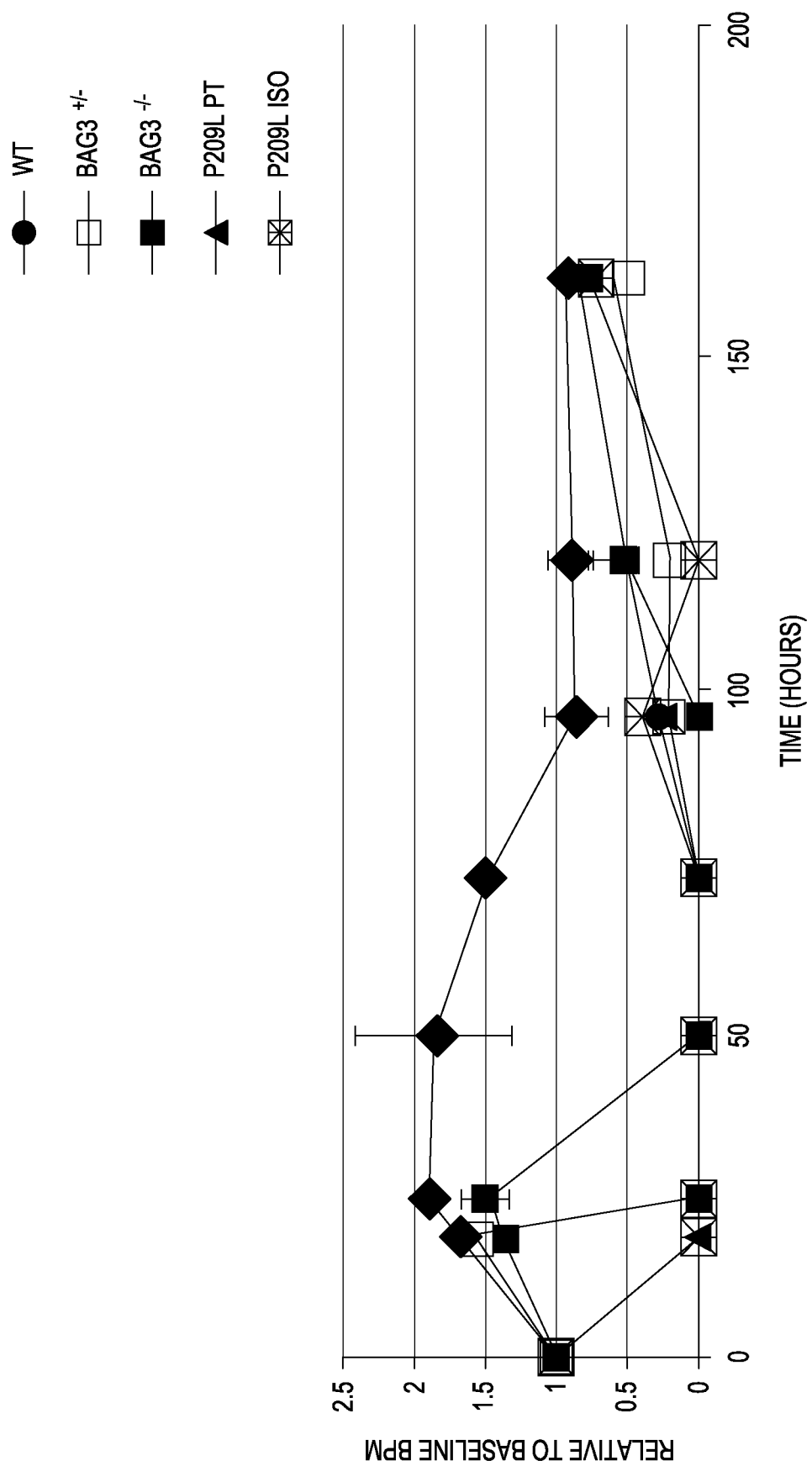
FIG. 6 is a line graph showing the effect of proteasome inhibitor MG132 on beat rate of $BAG3^{+/-}$ and $BAG3^{-/-}$ and $BAG3^{P209L}$ iPS-CMs.
Figure 7:
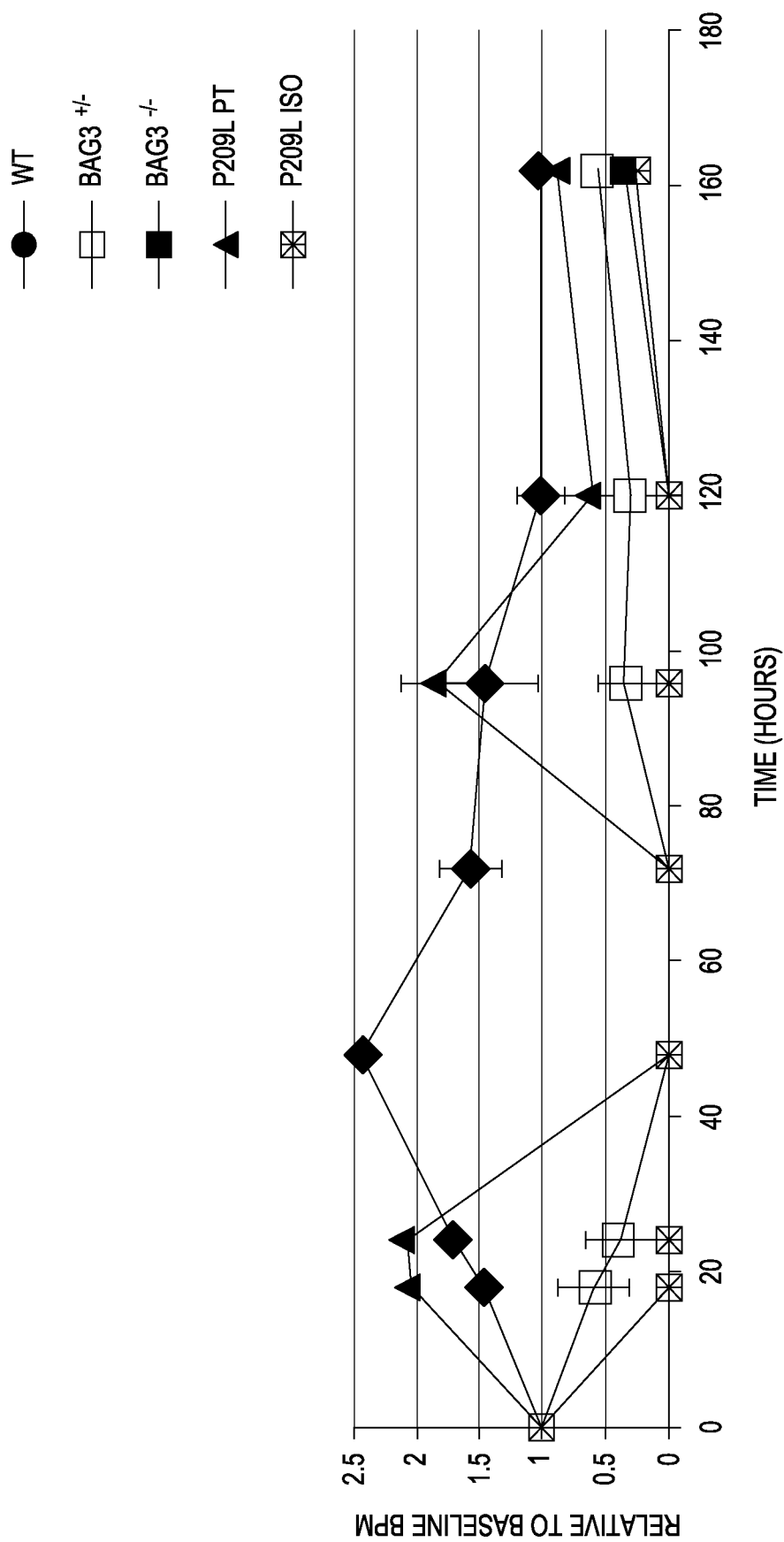
FIG. 7 is a line graph showing the effect of proteasome inhibitor bortezomib on beat rate of $BAG3^{+/-}$ and $BAG3^{-/-}$ and $BAG3^{P209L}$ iPS-CMs.

The beat rate was also measured for the various BAG3 mutant cell lines treated with the proteasome inhibitor MG132 (1 μM) (FIG. 6) or bortezomib (100 nM) (FIG. 7) using video microscopy. (Maddah et al (2015) Stem Cell Reports 4:1-11). Both the heterozygous and homozygous iPS-CM populations had a much more significant response to the proteasome inhibitors than the WT iPS-CM population, and essentially the cells stopped beating shortly after treatment with either MG132 or bortezemib. The BAG3 mutant cell lines returned to the baseline beat rate after recovering for approximately 5 days without dosage of the respective proteasome inhibitor. (FIGS. 6, 7).

Example 5: Sarcomeric Disarray Following Treatment of BAG3 Mutant Cells with Proteosome Inhibitors Using transient transfection of ACTININ2-Kate, BAG3-dependent sarcomeric disarray phenotypes in response to protease inhibitors were observed in living iPS-CMs for several days. By inducing stress with bortezomib, a proteasome inhibitor and approved chemotherapy agent, sarcomeric disarray was induced in living BAG3$^{-/-}$ iPS-CMs tracked over several days.

Bortezomib (0.1 μM) was added to the media of the BAG3$^{-/-}$ iPS-CMs for two days, and the cells imaged repetitively, both during and following introduction of the agent. Sarcomere alignment and scoring in live iPS-CMs expressing transgenic ACTININ2-Kate was determined by repetitive imaging. The BAG3$^{-/-}$ cells demonstrated a markedly increased response to bortezomib that is apparent at 2 days.

Example 6: Measurement of Contractility in ISOGENIC iPS-CM Populations

The measurement of cell contractility as a measurement of cardiotoxicity of proteasome inhibitors is particularly important, as they are actively used in cancer therapy. (Bockorny M et al. (2012) *Acta Haematol* 128:244-7; Watanabe M et al., (2014) *Toxicology* 322:43-50.

A marked inhibition of contractility was induced by treating isogenic iPS-CMs having a BAG3 with a proteasome inhibitor. This was shown for the BAG3+/- cell populations, the BAG3-/- cell populations and the BAG3 cell populations having the P209L isogenic point mutation. This phenotype is striking and partially reversible in each of the tested BAG3 mutant cell populations.

Figure 8:
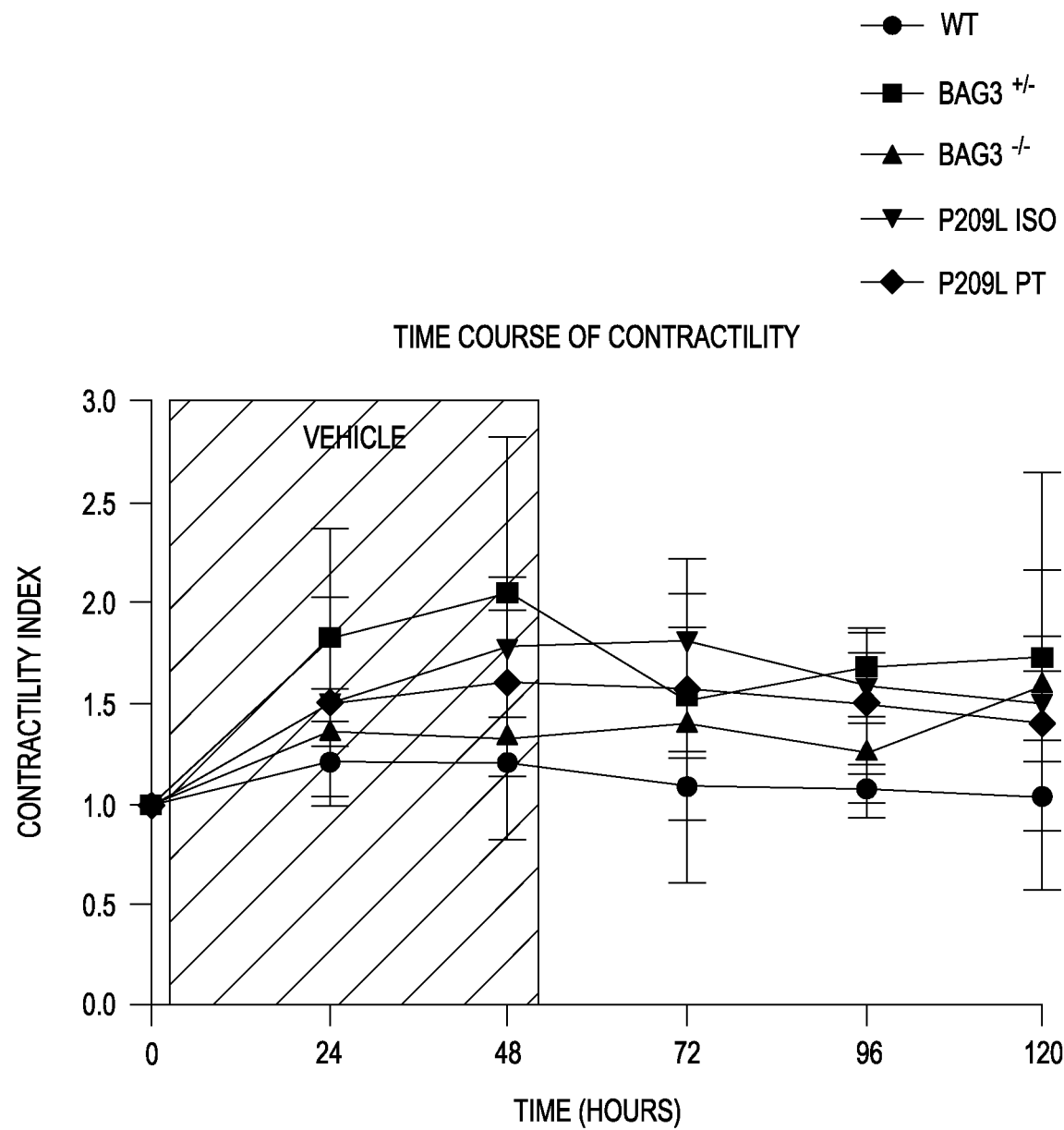
FIG. 8 is a line graph showing the time course of contractility in WT and BAG3 mutant iPS-CM.

Cell populations with the tested BAG3 mutations were created as described in the Example 2. Human iPSC-derived cardiomyocytes were differentiated using the protocol described in US Pat App. 20130189785 (See also Lian et al (2012) *Nat Protoc.* 2013 January; 8(1):162-75). Cryopreserved cardiomyocytes produced from isogenic iPSC lines containing a homozygous BAG3 KO mutation, a heterozygous BAG3 KO mutation, two different heterozygous P209L mutations (one patient-derived (P209L pt) and the other engineered from isogenic WT control (P209L iso)) or heterozygous vector insertion (as a negative control) were thawed directly into Matrigel-coated 6-well plates containing basal media supplemented with Rock inhibitor. After 4-6 days recovery in basal media, the cells were re-plated into 48 or 96-well plates at confluent density. After another 5-10 days of maintenance in basal media, the baseline physiologic parameters were measured by automated video microscopy and image analysis (PULSE system, Cellogy, Palo Alto, Calif.). Contractility (based on contraction peak height) was measured as described by Maddah et al (2015) *Stem Cell Reports* 2015 Apr. 14; 4(4):621-31, and plotted for WT ISP-CM and the various BAG3 mutant isogenic cells (FIG. 8).

An automated video microscopy system (Cellogy Pulse) was used for serial measurements of iPS-CM contractility every 24 hours after exposure to vehicle control (DMSO 0.01%) or bortezomib (0.1 µM). Cells were exposed to drug for 48 hours after which they were allowed to recover in basal media. Contractility index represents the contraction peak height at each time point normalized to the baseline value for each replicate. Mean values of triplicate samples are plotted with standard deviation, * p<0.05 compared to vehicle control via t-test.

Figure 10A:
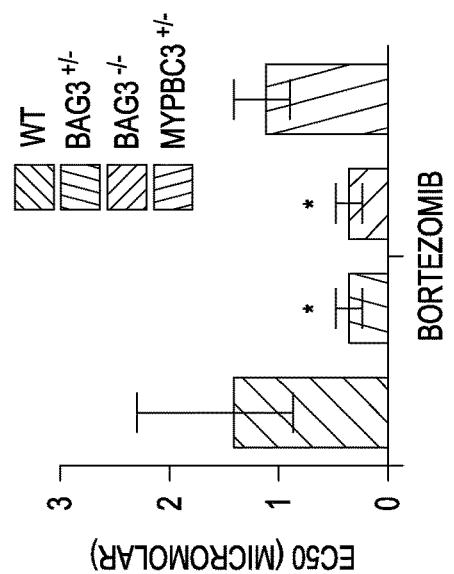
FIGS. 10a-10c are bar graphs comparing the drug effect of bortezomib, carfilzomib and doxorubicin on WT, BAG3 mutant, and MYPBC3 mutant iPS-CM contractility
Figure 10B:
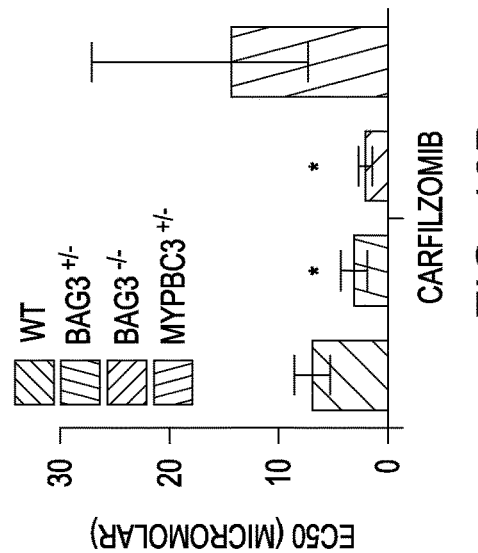
Figure 10C:
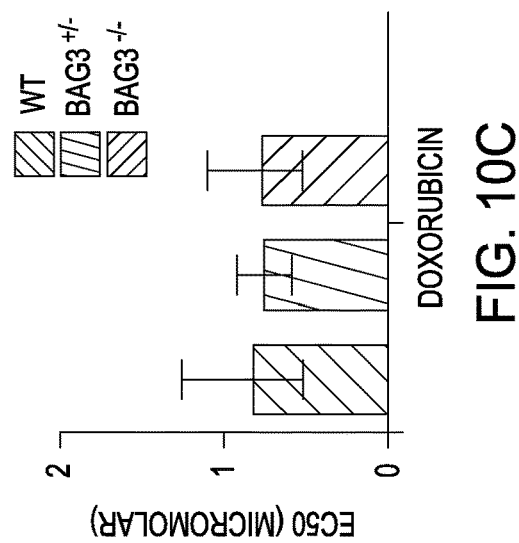
Figures 11A, 11B, 11C:
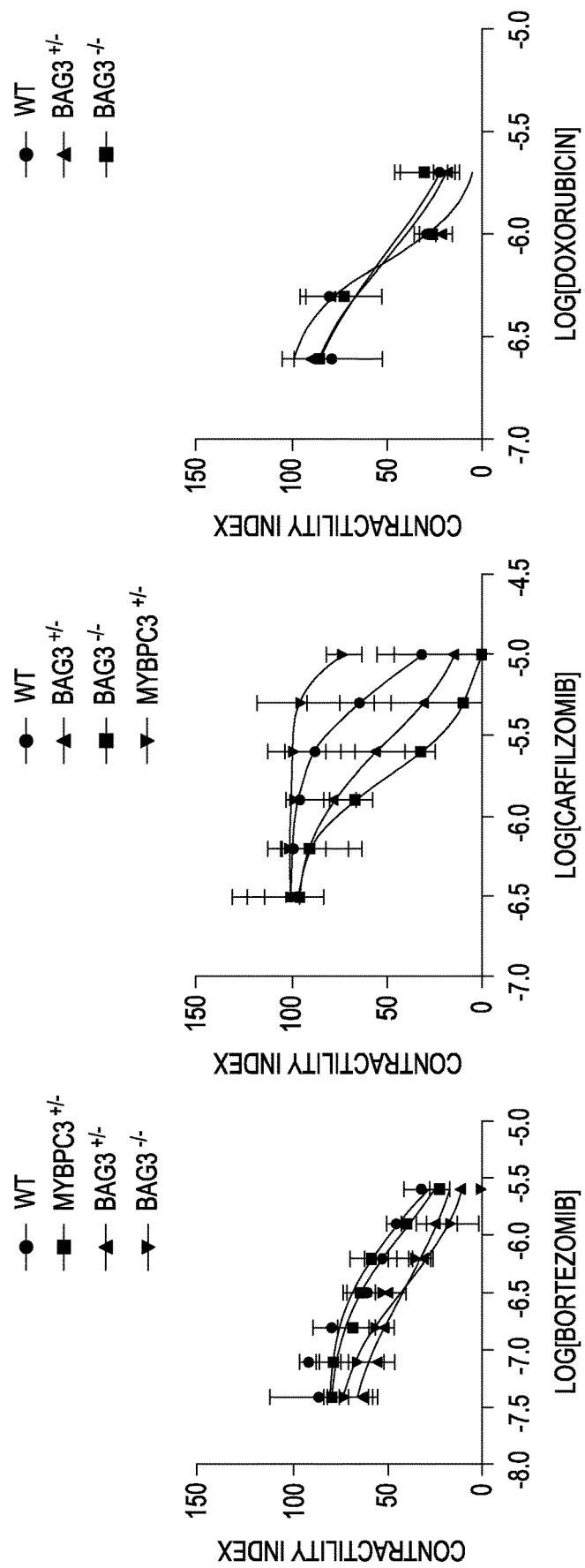
FIGS. 11a-11c are a series of graphs showing the effect of different drugs on contractility of WT, BAG3 mutant, and MYPBC3 mutant iPS-CM.

Doxorubicin toxicity was measurable by a decrease in contractility in wild-type as well as BAG3 mutant cells (FIG. 11c), and there was not a statistically significant increased toxicity in BAG3 mutant iPS-CM as compared to WT iPS-CM for doxorubicin (FIGS. 10a-c and FIGS. 11a-c). A statistically significant decrease in iPS-CM contractility was observed after a single exposure of the BAG3+11 and −/− mutants to the proteasome inhibitors bortezomib and carfilzomib (FIGS. 11a-c). All data were plotted as mean and standard deviation of replicates.

TABLE 1

EC50 values for cardio-toxicity of proteasome inhibitors and doxorubicin.

|  | WT | BAG3+/− | BAG3−/− | MYBPC3+/− |
|---|---|---|---|---|
| Bortezomib-Contractility | | | | |
| EC50 | 1.4 µM | 0.34 µM | 0.35 µM | 1.1 µM |
| 95% C.I. | 0.88-2.3 µM | 0.25-0.46 µM | 0.25-0.49 µM | 0.9-1.4 µM |
| Carfilzomib-Contractility | | | | |
| EC50 | 6.6 µM | 2.9 µM | 1.7 µM | 14 µM |
| 95% C.I. | 5.2-8.4 µM | 2.1-4 µM | 1.5-2 µM | 7.2-27.3 µM |
| Doxorubicin-Contractility | WT | BAG3+/− | BAG3−/− | |
| EC50 | 0.81 µM | 0.74 µM | 0.76 µM | |
| 95% C.I. | 0.52-1.26 µM | 0.61-0.9 µM | 0.53-1.1 µM | |

Figure 9:
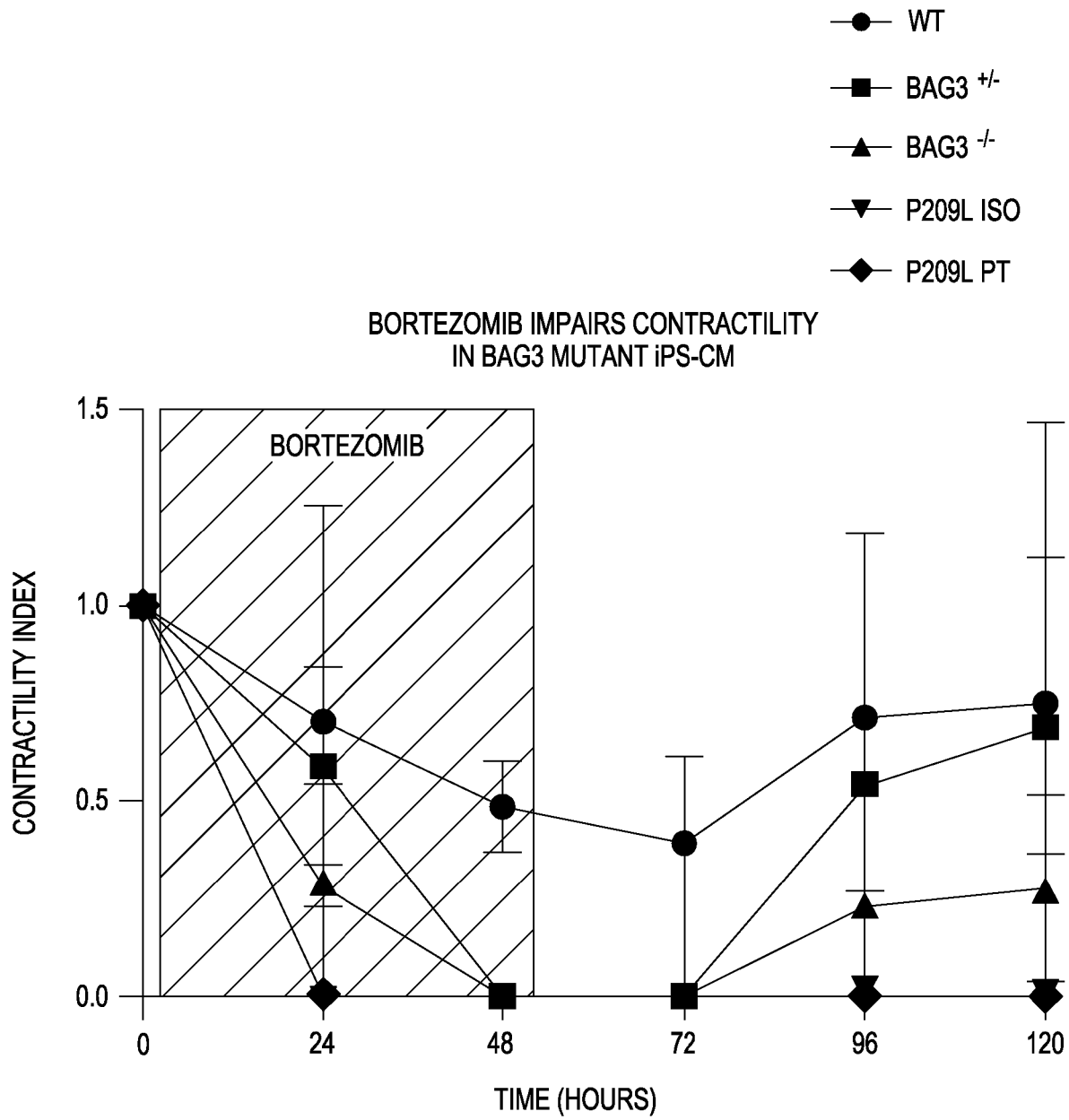
FIG. 9 is a line graph showing the effect of bortezomib on contractility in WT vs. BAG3 mutant iPS-CM.

The data demonstrates that a single exposure to low-dose bortezomib led to a severe decrease in contractility for all BAG3 mutant iPS-CM as compared to WT controls (FIG. 9). The effect on contractility was observed with greatest effect after approximately two days after drug administration. The contractility of mutant BAG3 lines was found to partially recover following a 5-day reprieve from the drug. (FIG. 9).

Example 7: Specificty of the Effect of Proteosome Inhibitors

To ensure the drug effects seen on the BAG3 mutant iPS-CM were related to the effect of proteasome inhibition of the agents such as bortezomib, dose response assays for cell contractility were performed using WT iPS-CM, BAG3 mutant iPS-CM, and MYPBC3 mutant iPS-CM. MYPBC3 is commonly mutated in cardiomyopathy, and was found to interact with BAG3 in preliminary affinity-purification mass spectrometry experiments, suggesting that it could be a relevant client protein for the BAG3 chaperone complex. The MYPBC3 mutant line was generated as a negative control using a modification of the same knockout vector for targeting BAG3, with MYBPC3 specific TALENs. To confirm specificity of drug activity and toxicity, the assay was also performed with doxorubicin, a well-known cardiotoxic chemotherapy agent.

A contractility index for the iPS-CM was measured after 48 hours of exposure to various concentrations of bortezomib, carfilzomib, and doxorubicin, and cells were allowed to recover for five additional days in basal media. The EC50 was calculated for the effects of each drug on iPS-CM contractility (FIG. 10a-c, Table 1). For inhibition of contractility by bortezomib and carfilzomib, the EC50 was significantly lower in both BAG3+/− and BAG3−/− cells compared to WT, but not MYPBC3+/−(FIG. 10a-c, Table 1).

While this invention is satisfied by aspects in many different forms, as described in detail in connection with the preferred invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. All references cited herein are incorporated by their entirety for all purposes. In the claims that follow, unless the term "means" is used, none of the features or elements recited therein should be construed as means-plus-function limitations pursuant to 35 U.S.C. § 112, ¶6.

We claim:

1. A method of determining the risk of agent-induced toxicity in a patient population comprising:
   providing a panel of isogenic cell populations comprising muscle cells, muscle cell progenitors, or a combination thereof produced from differentiated induced pluripotent stem cells, wherein the isogenic cell populations comprise mutations and/or polymorphisms of BAG3;
   contacting said panel of isogenic cell populations with an agent; and
   detecting ex vivo live cellular activity associated with toxicity resulting from contact with the agent in any of the isogenic cell populations, thereby detecting genotypes of BAG3 that are associated with an increased risk of agent-induced toxicity resulting from the BAG3 genotype in the patient population.

2. The method of claim 1, wherein the agent is a proteasome inhibitor.

3. The method of claim 2, wherein the agent inhibits autophagy in the cell populations.

4. The method of claim 1, wherein the muscle cells or muscle cell progenitors are skeletal muscle cells or skeletal muscle cell progenitors.

5. The method of claim 1, wherein the muscle cells or muscle cell progenitors are cardiomyocytes or cardiomyocyte progenitors.

6. The method of claim 1, wherein the ex vivo cellular activity is sarcomeric disarray or contractility by the muscle cells, muscle cell progenitors, or a combination thereof.

7. The method of claim 1, wherein the ex vivo cellular activity is detected over time.

* * * * *

UNITED STATES PATENT AND TRADEMARK OFFICE
CERTIFICATE OF CORRECTION

PATENT NO. : 11,020,463 B2  
APPLICATION NO. : 15/750495  
DATED : June 1, 2021  
INVENTOR(S) : Conklin et al.

Page 1 of 1

It is certified that error appears in the above-identified patent and that said Letters Patent is hereby corrected as shown below:

On the Title Page

In Item (73), in "Assignee", in Column 1, Lines 1-4, delete "The J. David Gladstone Institutes, San Francisco, CA (US), a testamentantary trust established under the Will of J. David Gladstone;" and insert --The J. David Gladstone Institutes, a testamentary trust established under the Will of J. David Gladstone, San Francisco, CA (US);-- therefor Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*